United States Patent
Chappuis

(10) Patent No.: US 12,161,556 B2
(45) Date of Patent: Dec. 10, 2024

(54) INTERNAL PEDICLE INSULATOR

(71) Applicant: CHAP-MED, INC., Destin, FL (US)

(72) Inventor: James L. Chappuis, Destin, FL (US)

(73) Assignee: CHAP-MED, INC., Destin, FL (US)

(*) Notice: Subject to any disclaimer, the term of this patent is extended or adjusted under 35 U.S.C. 154(b) by 0 days.

(21) Appl. No.: 18/086,823

(22) Filed: Dec. 22, 2022

(65) Prior Publication Data

US 2023/0127165 A1    Apr. 27, 2023

Related U.S. Application Data

(63) Continuation of application No. 16/656,067, filed on Oct. 17, 2019, now Pat. No. 11,540,920.

(51) Int. Cl.
*A61F 2/44* (2006.01)
*A61F 2/30* (2006.01)
*A61F 2/46* (2006.01)

(52) U.S. Cl.
CPC ........ *A61F 2/30749* (2013.01); *A61F 2/4455* (2013.01); *A61F 2/4611* (2013.01); *A61F 2002/30158* (2013.01); *A61F 2002/30261* (2013.01); *A61F 2002/30322* (2013.01); *A61F 2002/3069* (2013.01); *A61F 2002/30828* (2013.01); *A61F 2002/30894* (2013.01)

(58) Field of Classification Search
CPC ............ A61B 17/7094; A61B 17/8095; A61B 17/8872; A61B 17/84–8695; A61F 2002/3069; A61F 2/4611
See application file for complete search history.

(56) References Cited

U.S. PATENT DOCUMENTS

| | | | |
|---|---|---|---|
| 5,501,557 A | 3/1996 | Wakai | |
| 5,688,090 A | 11/1997 | Miyamoto | |
| 5,749,688 A | 5/1998 | Wakai | |
| 6,093,207 A | 7/2000 | Pisharodi | |
| 6,306,156 B1 | 10/2001 | Clark | |
| 6,485,517 B1 | 11/2002 | Michelson | |
| 6,506,008 B2 | 1/2003 | Merkli | |
| 6,767,350 B1 | 7/2004 | Lob | |
| 7,083,621 B2 | 8/2006 | Shaolian et al. | |
| 7,338,500 B2 | 3/2008 | Chappuis | |
| 7,534,265 B1* | 5/2009 | Boyd | A61F 2/446 623/17.11 |
| 7,686,555 B1 | 3/2010 | Larson et al. | |
| 8,361,152 B2* | 1/2013 | McCormack | A61B 17/8811 623/17.15 |
| 8,900,236 B2 | 12/2014 | Chappuis | |

(Continued)

*Primary Examiner* — Eduardo C Robert
*Assistant Examiner* — Steven J Cotroneo
(74) *Attorney, Agent, or Firm* — Perilla Knox & Hildebrandt LLP; Stephanie Davy-Jow; Bradley K. Groff

(57) ABSTRACT

A pedicle insulator implant is designed to protect the nerves and surrounding tissue from injury by pedicle screws or other surgical devices and instruments. The implant is configured to shield a fixture, reduce nerve root irritation, and diminish loosening of the fixture, when the fixture is implanted into the void of a target site. The implant includes features for stabilizing and securing the implant within the void at the target site. For example, in one embodiment, the implant includes one or more ridges and one or more teeth sections that stabilize the implant against rotational and extractive forces that could disturb the implant.

20 Claims, 21 Drawing Sheets

(56) References Cited

U.S. PATENT DOCUMENTS

| | | |
|---|---|---|
| 8,956,394 B1 | 2/2015 | McDonnell |
| 9,381,049 B2 | 7/2016 | McCormack |
| 9,888,911 B2* | 2/2018 | Siegal ................... A61B 17/025 |
| 10,441,430 B2 | 10/2019 | Ludwig |
| 10,575,885 B2* | 3/2020 | Kim ....................... A61B 17/70 |
| 10,588,750 B2* | 3/2020 | Souza ................. A61B 17/7055 |
| 2002/0143401 A1 | 10/2002 | Michelson |
| 2004/0176767 A1 | 9/2004 | Bickley |
| 2004/0267277 A1 | 12/2004 | Zannis et al. |
| 2005/0216012 A1* | 9/2005 | Willmen ............... A61B 17/686 |
| | | 606/104 |
| 2005/0240194 A1 | 10/2005 | Chappuis |
| 2006/0095040 A1 | 5/2006 | Schlienger |
| 2007/0118131 A1 | 5/2007 | Gooch |
| 2007/0162027 A1 | 7/2007 | Chappuis |
| 2007/0219553 A1 | 9/2007 | Chappuis |
| 2008/0133007 A1* | 6/2008 | Donnelly ............... A61F 2/0811 |
| | | 606/232 |
| 2008/0161864 A1* | 7/2008 | Beck ..................... A61F 2/0811 |
| | | 606/326 |
| 2008/0221623 A1 | 9/2008 | Gooch |
| 2008/0221624 A1* | 9/2008 | Gooch ................... A61B 17/70 |
| | | 606/302 |
| 2010/0174320 A1* | 7/2010 | Truckai ................. A61B 17/70 |
| | | 606/279 |
| 2010/0198258 A1 | 8/2010 | Heaven |
| 2011/0106177 A1* | 5/2011 | Lewis .................. A61B 17/686 |
| | | 606/305 |
| 2011/0144766 A1 | 6/2011 | Kale |
| 2011/0238124 A1 | 9/2011 | Richelsoph |
| 2012/0203226 A1 | 8/2012 | Schlienger et al. |
| 2013/0006278 A1* | 1/2013 | Mayer ................ A61B 17/8645 |
| | | 606/151 |
| 2014/0067063 A1 | 3/2014 | Bonutti |
| 2015/0045841 A1 | 2/2015 | Oglaza et al. |
| 2015/0105830 A1 | 4/2015 | Biedermann et al. |
| 2015/0150557 A1 | 6/2015 | Tsai et al. |
| 2015/0342644 A1 | 12/2015 | Chappuis |
| 2016/0038206 A1 | 2/2016 | McDonnell |
| 2016/0074072 A1 | 3/2016 | McDonnell et al. |
| 2016/0128735 A1 | 5/2016 | Suddaby |
| 2017/0128100 A1 | 5/2017 | Jones et al. |
| 2017/0215934 A1 | 8/2017 | McDonnell |

* cited by examiner

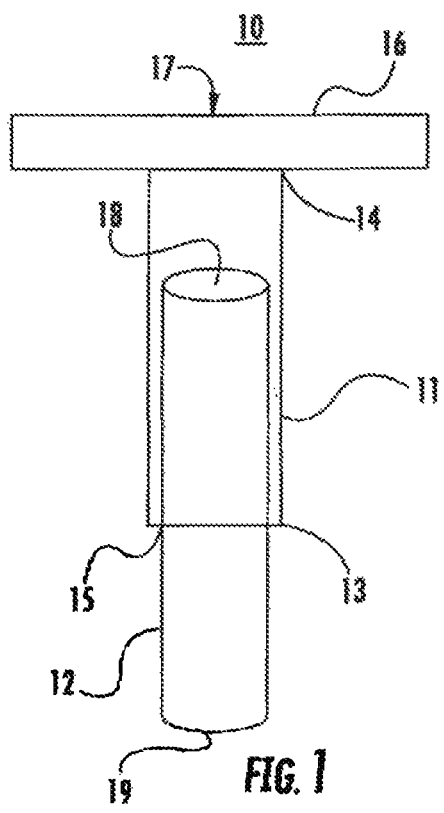
FIG. 1
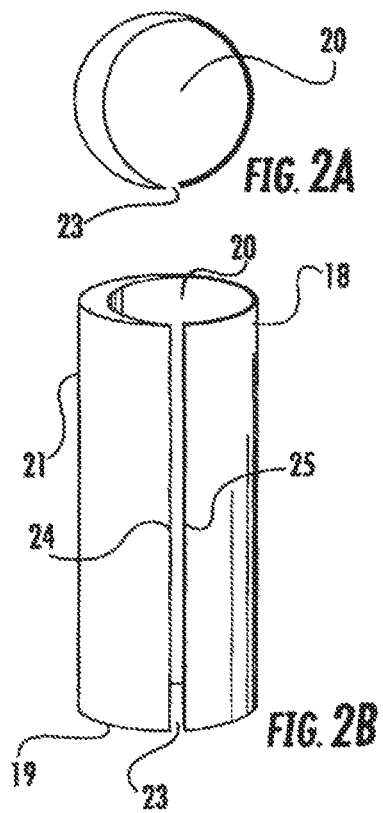
FIG. 2A
FIG. 2B
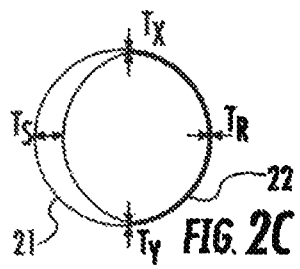
FIG. 2C
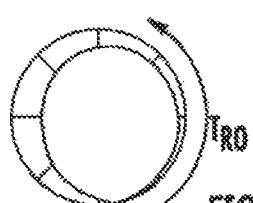
FIG. 2E
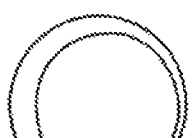
FIG. 2G
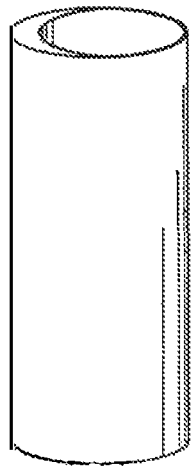
FIG. 2D
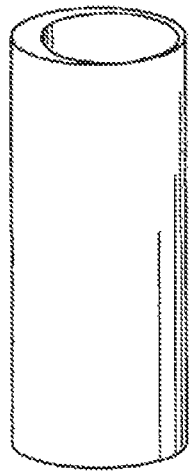
FIG. 2F
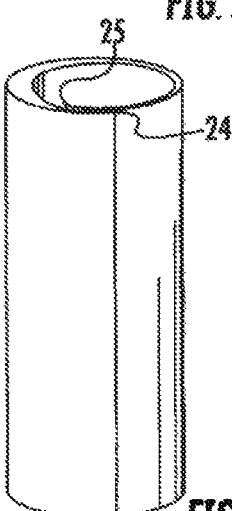
FIG. 2H

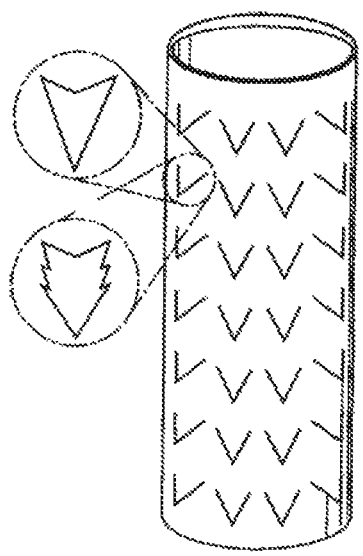
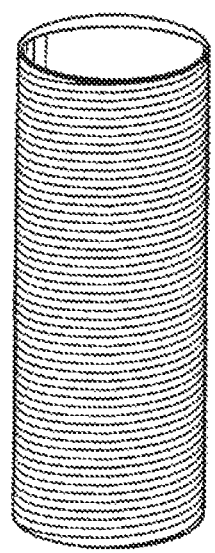
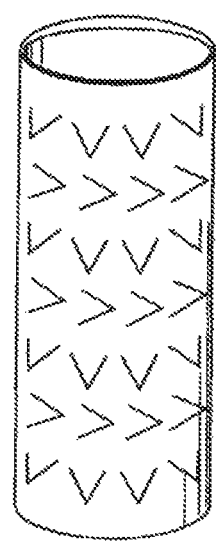
FIG. 3A   FIG. 3B   FIG. 3C
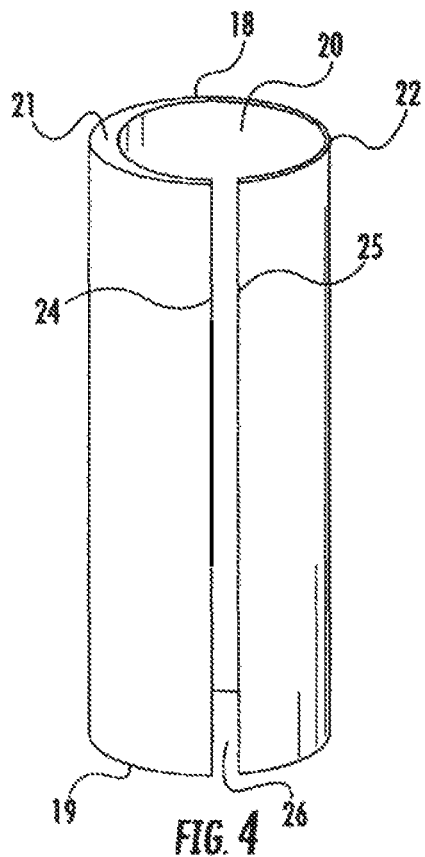
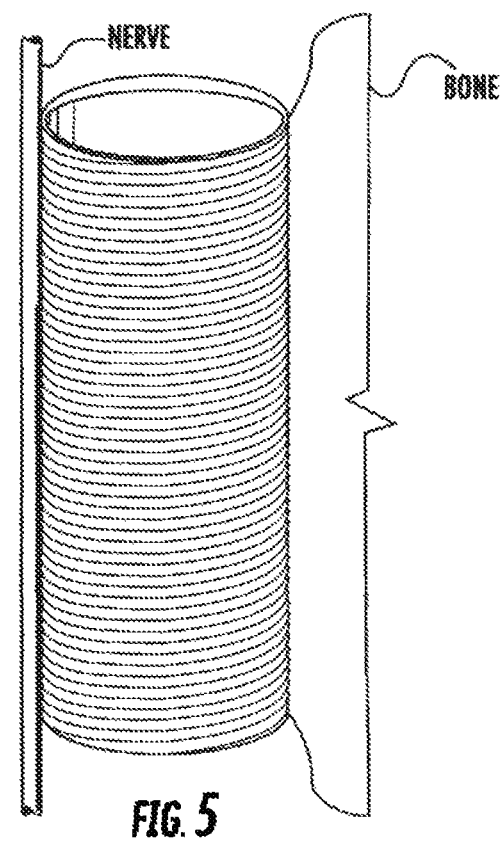
FIG. 4   FIG. 5

INTERNAL PEDICLE INSULATOR

CROSS-REFERENCE TO RELATED APPLICATIONS

This application is a continuation of U.S. Non-Provisional patent application Ser. No. 16/656,067 filed Oct. 17, 2019, the entirety of which is hereby incorporated herein by reference for all purposes.

This application is also related to: U.S. patent application Ser. No. 16/511,946, filed Jul. 15, 2019, entitled "INTERNAL PEDICLE INSULATOR," which is a continuation of U.S. patent application Ser. No. 15/975,308, filed May 9, 2018, now U.S. Pat. No. 10,390,860, entitled "INTERNAL PEDICLE INSULATOR," which is a continuation of U.S. patent application Ser. No. 14/723,620, filed May 28, 2015, now U.S. Pat. No. 9,993,268, entitled "INTERNAL PEDICLE INSULATOR" which claims the benefit of and priority to U.S. Provisional Patent Application No. 62/003,978, entitled "INTERNAL PEDICLE INSULATOR", filed May 28, 2014; and U.S. patent application Ser. No. 11/712,257, filed Feb. 28, 2007, now U.S. Pat. No. 8,728,132, entitled "INTERNAL PEDICLE INSULATOR APPARATUS AND METHOD OF USE," which is a continuation in part of U.S. Pat. No. 7,338,500, filed Apr. 20, 2005, entitled "INTERNAL PEDICLE INSULATOR APPARATUS AND METHOD OF USE."

The contents of the above referenced applications are incorporated herein by reference in their entireties.

TECHNICAL FIELD

The present technology relates generally to surgical instruments and tools. In particular, pedicle insulator assemblies and methods of insertion are described.

BACKGROUND

Spinal fusion typically involves the removal of damaged disc material between two adjacent vertebrae and the subsequent insertion of one or more interbody devices into the emptied disc space, either using an anterior or a posterior approach. In order to ensure primary stability, the surgeon usually adopts a fixation system that is anchored to the spine by means of orthopedic screws implanted into the pedicles of the vertebrae that are to be fused together. The single screws are connected together by means of rigid or semi-rigid rods, which are conveniently housed within a transversal hole provided in the screw head.

Since the FDA approval of pedicle screws, approximately 200,000 instrumented fusions occur each year in the US. There is very limited tolerance between the pedicle screw and the nerve root with the inferomedial wall of the pedicle (approx. 1-2 mm). Current minimally invasive techniques increase risk of malposition. The pedicle screw may be inserted off center, such as, for example, too medial, which may impinge on the associated nerve root causing pain. This requires a repositioning of the screw. However, even after repositioning there may be an effect on the pedicle wall, which can still cause nerve root irritation. Such procedures are also susceptible to loosening of the screw.

BRIEF SUMMARY

Embodiments of the present technology are directed to an internal pedicle insulator implant assemblies and related methods. In this regard, an exemplary embodiment of an internal pedicle insulator implant comprises: a cylindrical wall defining an interior cavity and having a first end and a second end, the cylindrical wall comprising a smooth, non-threaded segment, a rough surface segment, or combinations thereof. In some embodiments, one segment of the wall is of a greater thickness than other segments of the wall; whereby the pedicle insulator implant shields a pedicle screw that is implanted into the vertebral body and reduces nerve root irritation and diminishes the loosening of the pedicle screw.

According to a first aspect, an implant for stabilizing a surgical fixture including: A) a proximate end and a distal end; B) a substantially smooth channel surface symmetrically bisected by a medial axis extending longitudinally between the proximate end and the distal end, the substantially smooth channel surface terminating at a left edge and a right edge; C) one or more ridges symmetrically oriented along the medial axis and forming a ridge surface opposite the substantially smooth channel surface; D) a left teeth section extending outwardly from the left edge at an acute left runner angle from a horizontal plane passing through the left edge and the right edge; and E) a right teeth section extending outwardly from the right edge at an acute right runner angle from the horizontal plane.

According to a second aspect, the implant of the first aspect or any other aspect, wherein the left teeth section includes one or more teeth, wherein each tooth of the one or more teeth includes a generally trapezoidal prism shape.

According to a third aspect, the implant of the first aspect or any other aspect, wherein the ridge surface extends longitudinally between the proximate end and the distal end.

According to a fourth aspect, the implant of the first aspect or any other aspect, wherein each ridge of the one or more ridges includes a fixation surface that is disposed towards the proximate end and that is oriented orthogonal to the medial axis.

According to a fifth aspect, the implant of the first aspect or any other aspect, wherein a length of the medial axis between the proximate end and the distal end is about 15 mm to 50 mm.

According to a sixth aspect, the implant of the first aspect or any other aspect, wherein the implant further includes a tip near the distal end.

According to a seventh aspect, the implant of the sixth aspect or any other aspect, wherein the implant includes a sloped surface between a ridge of the ridge section to the tip.

According to a seventh aspect, the implant of the first aspect or any other aspect, wherein: A) the implant further includes a proximate face located near the proximate end of the implant, the proximate face including a body section and the left teeth section and the right teeth section; B) the body section includes a curved top surface and a curved bottom surface; C) the curved bottom surface terminates at a left end point and a right end point, wherein: 1) a bottom surface of the left teeth section extends outwardly from the left end point at a left runner angle from a horizontal plane passing through the left end point and the right end point; and 2) a bottom surface of the right teeth section extends outwardly from the right end point at a right runner angle from the horizontal plane.

According to a ninth aspect, the implant of the first aspect or any other aspect, wherein the angle of the left runner angle is approximately 0-30°.

According to a tenth aspect, the implant of the ninth aspect or any other aspect, wherein the angle of the acute right runner angle is substantially similar to the angle of the acute left runner angle.

According to an eleventh aspect, a method for stabilizing a surgical fixture including: A) creating a void in a target site; B) deploying an implant into the void of the target site, the implant including: 1) a proximate end and a distal end; 2) a substantially smooth channel surface symmetrically bisected by a medial axis extending longitudinally between the proximate end and the distal end, the substantially smooth channel surface terminating at a left edge and a right edge; 3) one or more ridges symmetrically oriented along the medial axis and forming a ridge surface opposite the substantially smooth channel surface; and 4) wherein the implant is configured to shield a fixture, reduce nerve root irritation, and diminish loosening of the fixture, when the fixture is implanted into the void of the target site.

According to a twelfth aspect, the method of the eleventh aspect or any other aspect, wherein the implant further includes: A) a left teeth section extending outwardly from the left edge at an acute left runner angle from a horizontal plane passing through the left edge and the right edge; and B) a right teeth section extending outwardly from the right edge at an acute right runner angle from the horizontal plane.

According to a thirteenth aspect, the method of the twelfth aspect or any other aspect, wherein the one or more ridges, the left teeth section, and the right teeth section reduce a tendency of the fixture to toggle and increase a pullout strength of the fixture.

According to a fourteenth aspect, the method of the eleventh aspect or any other aspect, wherein the left teeth section includes one or more teeth, wherein each tooth of the one or more teeth includes a generally trapezoidal prism shape.

According to a fifteenth aspect, the method of the eleventh aspect or any other aspect, wherein: A) the ridge surface extends longitudinally between the proximate end and the distal end; and B) each ridge of the one or more ridges includes a fixation surface that is disposed towards the proximate end and that is oriented orthogonal to the medial axis.

According to a sixteenth aspect, the method of the eleventh aspect or any other aspect, wherein a length of the medial axis between the proximate end and the distal end is about 15 mm to 50 mm.

According to a seventeenth aspect, the method of the eleventh aspect or any other aspect, wherein the method further includes: A) a tip near the distal end; and B) a sloped surface between a ridge of the ridge section to the tip.

According to an eighteenth aspect, the method of the eleventh aspect or any other aspect, wherein the fixture is a pedicle screw.

According to a nineteenth aspect, the method of the eleventh aspect or any other aspect, wherein the implant is in contact with the fixture prior to and throughout deployment into the void of the target site.

According to a twentieth aspect, the method of the eleventh aspect or any other aspect, wherein the implant is deployed within the void of the target site prior to implantation of the fixture.

According to a twenty-first aspect, an implant for stabilizing a surgical fixture comprises an elongate body formed about an axis of revolution. The elongate body further comprises: a proximal end; a distal end; a channel surface extending between the proximal and distal ends; a ridged surface opposite the channel surface extending between the proximal and distal ends comprising one or more ridges; a first longitudinal runner and a second longitudinal runner adjacent the channel surface and extending between the proximal and distal ends; a first teeth section extending outwardly from the first longitudinal runner comprising one or more teeth; and a second teeth section extending outwardly from the second longitudinal runner comprising one or more teeth. Within the implant, the radial distance between the axis of revolution to the outermost point of the one or more teeth is greater than the radial distance between the axis of revolution and the apex of the one or more ridges.

According to a twenty-second aspect of the invention, the implant of the twenty-first aspect of the invention comprises a channel surface configured to receive a surgical implant.

According to a twenty-third aspect of the invention, the implant of the twenty-second aspect of the invention is configured to receive a pedicle screw.

According to a twenty-fourth aspect of the invention, the implant of the twenty-first aspect of the invention has ridges with an elliptical profile.

According to a twenty-fifth aspect of the invention, the implant of the twenty-first aspect of the invention has a tooth height of at least one of the teeth as measured from the runner is between about 0.5 mm and 5 mm.

According to a twenty-sixth aspect of the invention, the implant of the twenty-first aspect of the invention has teeth that are shaped differently from the ridges.

According to a twenty-seventh aspect of the invention, the implant of the twenty-first aspect of the invention has teeth with a longitudinal width that is less than the longitudinal width of the ridges.

According to a twenty-eighth aspect of the invention, an implant for stabilizing a surgical fixture comprises an elongate body having a curved shape about its longitude. The elongate body further comprises: a proximal end; a distal end; a channel surface extending between the proximal and distal ends having a first longitudinal edge and a second longitudinal edge; a first runner surface adjacent to the first longitudinal edge and a second runner surface adjacent to the second longitudinal edge; a ridged surface opposite the channel surface and extending between the proximal and distal ends wherein the ridge section comprises one or more ridges having a first geometry; a first teeth section extending outwardly from the first runner surface wherein the first tooth section comprises one or more teeth having a second geometry; and a second teeth section extending outwardly from the second runner surface, wherein the second tooth section comprises one or more teeth having a second geometry. The second and third geometries are different from the first geometry According to a twenty-ninth aspect of the invention, within the implant of the twenty-eighth aspect of the invention, the first and second teeth sections of the implant have the same geometry.

According to a thirtieth aspect of the invention, within the implant of the twenty-eighth aspect of the invention, the teeth in the first and second teeth sections of the implant have a smaller longitudinal width than the ridges within the ridge section.

According to a thirty-first aspect of the invention, within the implant of the twenty-eighth aspect of the invention, the first and second teeth sections of the implant have a greater radial height than the ridge section.

According to a thirty-second aspect of the invention, within the implant of the twenty-eighth aspect of the invention, the faces of the teeth closest the distal end of the implant are at a different angle form the faces of the ridges closest to the distal end of the implant relative to the channel surface.

According to a thirty-third aspect of the invention, within the implant of the thirty-second aspect of the invention, the faces of the teeth closest to the distal end of the implant do not align with the faces of the ridges closes to the distal end of the implant.

According to a thirty-fourth aspect of the invention, within the implant of the thirty-second aspect of the invention, the faces of the teeth closest to the proximal end of the implant align with the faces of the ridges closest to the proximal end of the implant.

According to a thirty-fifth aspect of the invention, an implant for stabilizing a surgical fixture comprises a generally elongate body of revolution, being revolved about an axis of revolution no more than 180 degrees and having a thickness. The body further comprises: a proximal end; a distal end; a channel surface formed on the face of the body nearest the axis of revolution; one or more ridges formed on the face of the body furthest from the axis of revolution; and one or more teeth formed at the longitudinal edges of the body and extending away from the axis of revolution. The teeth further comprise a first side surface adjacent to the channel and a second side surface opposite the first side surface that forms a crease with the ridge section.

According to a thirty-sixth aspect of the invention, within the implant according to the thirty-fifth aspect of the invention, the height of the teeth from the body of the revolution is greater than the height of the ridges from the body of revolution.

According to a thirty-seventh aspect of the invention, within the implant according to the thirty-fifth aspect of the invention, the teeth further comprise a sloping surface.

According to a thirty-eighth aspect of the invention, within the implant according to a thirty-seventh aspect of the invention, the sloping surface of the teeth is nearest the distal end.

According to a thirty-ninth aspect of the invention, within the implant according to a thirty-eighth aspect of the invention, the ridges comprise a sloping surface and the angle of the sloping surface of the ridges is different from the angle of the sloping surface of the teeth.

According to a fortieth aspect of the invention, within the implant according to a thirty-ninth aspect of the invention, the teeth and the ridges further comprise a flat surface normal to the channel surface.

Various embodiments of an internal pedicle insulator implant may further include, but are not limited to: 1) a pedicle insulator, wherein the pedicle insulator may be configured to shield a pedicle screw of the above description; 2) the pedicle insulator, wherein the pedicle insulator may include one or more shapes (e.g., solids of revolution); 3) the pedicle insulator, wherein the pedicle insulator may be configured to fixate its own insertion position and orientation upon insertion into a spine; 4) the pedicle insulator, wherein the pedicle insulator includes one or more of fixation ridges, fixation teeth, other fixation surfaces (e.g., for the purpose of fixating position and orientation); and 5) a pedicle insulator inserter, wherein the pedicle insulator inserter may be configured to deploy the pedicle insulator. Accordingly, it is an objective of the present technology to provide various embodiments of an internal pedicle insulator implant assembly for shielding a pedicle screw that is implanted into the vertebral body for reducing nerve root irritation and diminishing the loosening of the pedicle screw.

It is also another objective to provide methods for stabilizing a surgical fixture.

Other objectives and advantages of the present technology will become apparent from the following description taken in conjunction with the accompanying drawings wherein are set forth, by way of illustration and example, certain embodiments of the present technology. The drawings constitute a part of this specification and include exemplary embodiments of the present technology and illustrate various objects and features thereof.

BRIEF DESCRIPTION OF THE DRAWINGS

The accompanying drawings illustrate one or more embodiments and/or aspects of the disclosure and, together with the written description, serve to explain the principles of the disclosure. The components in the drawings are not necessarily to scale, emphasis instead being placed upon clearly illustrating the principles of the present technology. Wherever possible, the same reference numbers are used throughout the drawings to refer to the same or like elements of an embodiment, and wherein:

FIG. 1 is a perspective view of a pedicle insulator implant assembly, according to one embodiment.

FIG. 2A is a top view showing an embodiment of a cylindrical wall, according to one embodiment.

FIG. 2B is a side view of FIG. 2A, according to one embodiment.

FIG. 2C is a top view showing another embodiment of a cylindrical wall, according to one embodiment.

FIG. 2D is a side view of FIG. 2C, according to one embodiment.

FIG. 2E is a top view showing a further embodiment of a cylindrical wall, according to one embodiment.

FIG. 2F is a side view of FIG. 2E, according to one embodiment.

FIG. 2G is a top view showing a cylindrical wall, according to one embodiment.

FIG. 2H is a side view of FIG. 2G, according to one embodiment.

FIGS. 3A-3C are segment views showing various embodiments of a rough segment of a cylindrical wall, according to one embodiment.

FIG. 4 is a segment view showing, according to one embodiment, a cylindrical wall with a longitudinal slot extending from a first end to a second end, and having one segment of the cylindrical wall thicker than the other.

FIG. 5 is a segment view showing, according to one embodiment, a cylindrical wall having one segment of the cylindrical wall smooth and thicker in width as compared to an opposing segment which is rough and thinner in width. The smooth thicker segment is placed to protect the nerve from the pedicle screw.

DETAILED DESCRIPTION

Figure 6:
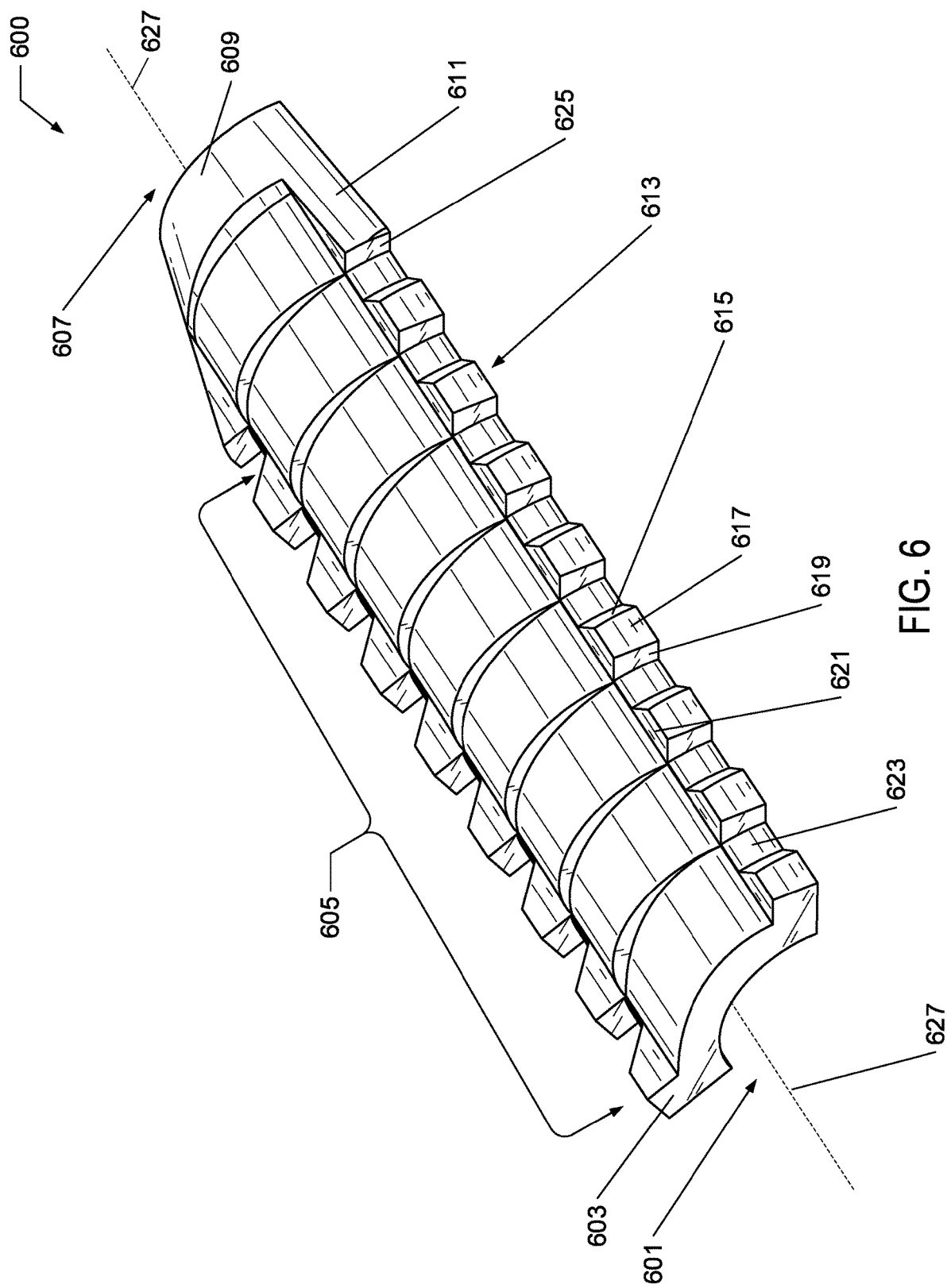
FIG. 6 is a perspective view of an exemplary pedicle insulator, according to one embodiment.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Any incorporation by reference is not intended to give a definitive or limiting meaning of a particular term. In the case of a conflict of terms, this document governs.

FIGS. 1-5 are described in:

U.S. patent application Ser. No. 16/511,946, filed Jul. 15, 2019, entitled "INTERNAL PEDICLE INSULATOR," which is a continuation of U.S. patent application Ser. No. 15/975,308, filed May 9, 2018, now U.S. Pat. No. 10,390,860, entitled "INTERNAL PEDICLE INSULATOR," which is a continuation of U.S. patent application Ser. No. 14/723,620, filed May 28, 2015, now U.S. Pat. No. 9,993,268, entitled "INTERNAL PEDICLE INSULATOR" which claims the benefit of and priority to U.S. Provisional Patent Application No. 62/003,978, entitled "INTERNAL PEDICLE INSULATOR", filed May 28, 2014; and U.S. patent application Ser. No. 11/712,257, filed Feb. 28, 2007, now U.S. Pat. No. 8,728,132, entitled "INTERNAL PEDICLE INSULATOR APPARATUS AND METHOD OF USE," which is a continuation in part of U.S. Pat. No. 7,338,500, filed Apr. 20, 2005, entitled "INTERNAL PEDICLE INSULATOR APPARATUS AND METHOD OF USE."

The above referenced applications, including descriptions therein of the FIGS. 1-5, are incorporated herein by reference in their entireties.

FIG. 6 illustrates a pedicle insulator 600. In various embodiments, the pedicle insulator 600 may include one or more shapes, wherein the one or more shapes may be solids of revolution. In one or more embodiments, the pedicle insulator 600 may be fabricated through additive manufacturing methods, such as 3D printing, through injection molding methods, through machining methods, or through a combination of methods. In at least one embodiment, the pedicle insulator 600 may include one or more materials including, but not limited to, 1) polyetheretherketone (PEEK); 2) titanium, and/or derivatives thereof; 3) stainless steel; 4) aluminum; 5) cobalt-chrome; 6) nickel alloy; 7) polyphenylsulfone (PPSU); 8) polysulfone (PSU); and 9) other materials suitable for use in additive manufacturing methods. In some embodiments, the pedicle insulator 600 may include one or more porous structures. For example, the one or more porous structures may be porous structures fabricated (e.g., 3D-printed, machined, or molded) from implant grade titanium and cobalt chromium alloy. In various embodiments, physical dimensions and geometry of the pedicle insulator 600 and any feature thereof may be determined, in part, by a geometry of an associated pedicle screw, a geometry of an associated insertion area (e.g., a pedicle insertion hole), and/or other geometric factors.

In various embodiments, the pedicle insulator 600 includes a proximate end 601 and a distal end 607. In one or more embodiments, the pedicle insulator 600 includes, but it not limited to, at least one teeth section 605. In at least one embodiment, the pedicle insulator 600 includes two of the teeth section 605. In various embodiments, the at least one teeth section 605 includes at least one tooth 613. In one or more embodiments, the tooth 613 may include a generally trapezoidal prism shape. Thus, the tooth 613 may include at least six surfaces, wherein at least one surface (e.g., a base surface) may be obfuscated and/or otherwise formed into the pedicle insulator 600.

In various embodiments, the tooth 613 may further include an outer tooth surface 617, wherein the orientation of the outer tooth surface 617 may be parallel to the insertion direction of the exemplary pedicle insulator. In various embodiments, the tooth 613 may include a tapered tooth surface 615, wherein the tapered tooth surface 615 may be generally oriented obtuse (e.g., in an interior angle) to the outer tooth surface 617. Orientation of the tapered tooth surface 615 is further illustrated herein in FIG. 22. In one or more embodiments, the tooth 613 includes a fixating tooth surface 619, wherein the orientation of the fixating tooth surface 619 may be orthogonal to the insertion direction of the exemplary pedicle insulator. In at least one embodiment, the orthogonal orientation of the fixating tooth surface 619 may increase the magnitude of a pullout force (e.g., in a direction parallel and opposite to the insertion direction) required to remove the exemplary pedicle insulator.

In various embodiments, the tooth 613 may include an outer channelization tooth surface 621, wherein the orientation of the outer channelization tooth surface 621 may be parallel to the insertion direction of the exemplary pedicle insulator. In one or more embodiments, the tooth 613 may further include an inner channelization tooth surface, such as is later illustrated in FIG. 8. In various embodiments, both inner and outer channelization surfaces may permit one or more exemplary pedicle insulators to fixate and secure their respective insertion position by increasing frictional forces along the respective inner and outer channelization surfaces.

In various embodiments, the pedicle insulator 600 may include at least one tooth gap 623. In one or more embodiments, the gap 623 may include the space of the runner 805, illustrated in FIG. 8, between the end of a tapered tooth surface 615 and the beginning of a fixating tooth surface 619. In at least one embodiment, the teeth section 605 includes a plurality of teeth 613 (such as, for example, 2-40 teeth 613) and a plurality of gaps 623 (such as, for example, 2-40 gaps 623).

In various embodiments, wherein the teeth section 605 includes teeth 613 and gaps 623. One or more of the teeth 613 and one or more of the gaps 623 may be located in a specific and repeated manner (e.g., within the teeth section 605). In one or more embodiments, the teeth section 605 may include, but is not limited to: 1) a fixed displacement distance between each of the one or more teeth located therein (e.g., teeth 613); 2) a fixed displacement distance between the one or more gaps located therein (e.g., gaps 623); and 3) determination of the above fixed displacement distances via alternating placement of one tooth followed immediately by placement of one gap. At least one embodiment of the above described arrangement may be illustrated in the teeth section 605 of FIG. 6.

In various embodiments, the pedicle insulator 600 may include a proximate face 603, wherein the proximate face 603 may be located at the proximate end 601. In one or more embodiments, the surface of the proximate face 603 may be flat and oriented orthogonal to the insertion direction of the exemplary pedicle insulator.

In various embodiments, the pedicle insulator 600 may include a tip 609. In at least one embodiment, the tip 609 may be located at the distal end 607. In one or more embodiments, the tip 609 may be located adjacent to the at least one teeth section 605. In various embodiments, the distal surface of the tip 609 may be generally flat. In at least one embodiment, the tip 609 further includes a tapered tip surface 611, wherein the direction of the tapered tip surface 611 (e.g., the taper direction) may be towards the distal end 607. In various embodiments, the tip 609 includes a generally curved wall, wherein the generally curved wall may include a tapering thickness.

In various embodiments, the tip 609 may include at least one tip fixation surface 625. In at least one embodiment, the tip fixation surface 625 may be oriented in a manner such that the magnitude of a pullout force (e.g., in a direction parallel and opposite to the insertion direction) required to remove the exemplary pedicle insulator is increased. In one or more embodiments, one or more of the tip fixation surface 625 may be placed at one or more locations along the tip 609. In at least one embodiment, FIG. 6 illustrates two respective placements of the tip fixation surface 625.

In at least one embodiment, the pedicle insulator 600 includes a medial axis 627. In one or more embodiments, the medial axis is orthogonal to the proximate face 603. In various embodiments, the pedicle insulator 600 may be symmetrically bisected along the medial axis 627.

Figure 7:
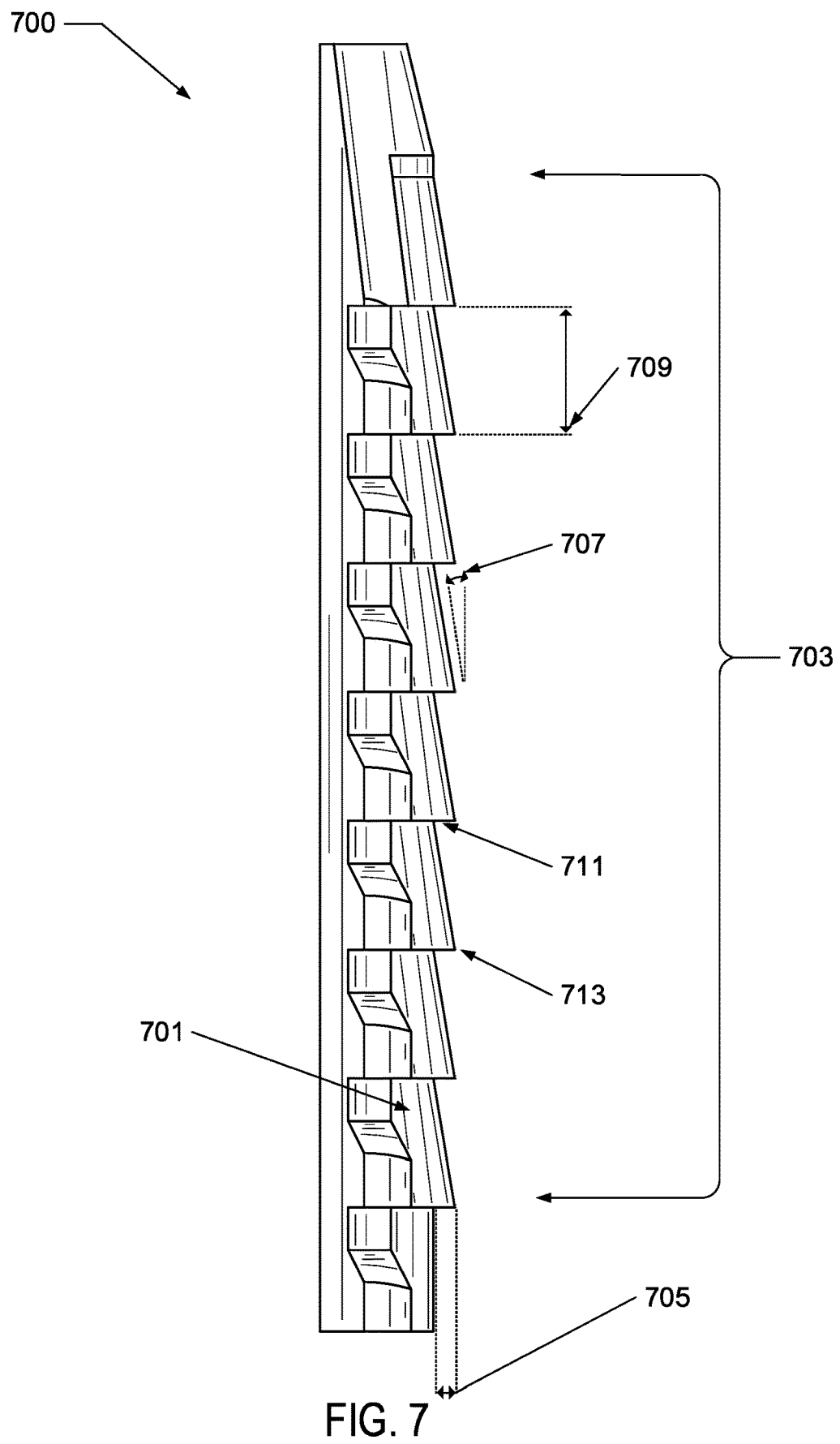
FIG. 7 is a side view of an exemplary pedicle insulator, according to one embodiment.

FIG. 7 illustrates a side view of an exemplary pedicle insulator 700. In various embodiments, the exemplary pedicle insulator 700 includes a ridge 701. In one or more embodiments, a ridge section 703 includes one or more ridges (e.g., ridges 701). In at least one embodiment, the ridge section 703 may include 2-7 ridges. In various embodiments, the ridge section 703 may be symmetrically oriented along the medial axis 627 of the pedicle insulator 600, each illustrated in FIG. 6.

In various embodiments, the ridge 701 may include a ridge fixation surface configured to increase the magnitude of a pullout force (e.g., in a direction parallel and opposite to the insertion direction) required to remove the pedicle insulator. In at least one embodiment, the fixation surface may be the fixation surface 1105 of FIG. 11, further described later herein.

In various embodiments, the ridge 701 includes a ridge bottom point 711 and a ridge apex 713. In various embodiments, the ridge 701 includes a ridge height 705. In at least one embodiment, the ridge height 705 may be between about 0.1 mm and about 2.0 mm. In various embodiments, the ridge height 705 may be determined by a ridge slope angle 707. In one or more embodiments, the ridge slope angle 707 may refer to the angle between the apex 713 and the bottom point 711. In at least one embodiment, the ridge projection angle 707 may be between about 5° and about 45°. In various embodiments, the ridge 701 includes a ridge length 709. In at least one embodiment, the ridge length 709 may be between about 0.25 mm and about 5 mm. In at least one embodiment the ridge length 709 may measure between about 0.01-0.5 mm, between about 0.5-1.0 mm, between about 1.0-1.5 mm, between about 1.5-2.0 mm, between about 2.0-2.5 mm, between about 3.0-3.5 mm, between about 3.5-4.0 mm, between about 4.5-5.0 mm, between about 5.0-5.5 mm, or between about 5.5-6.0 mm.

Figure 8:
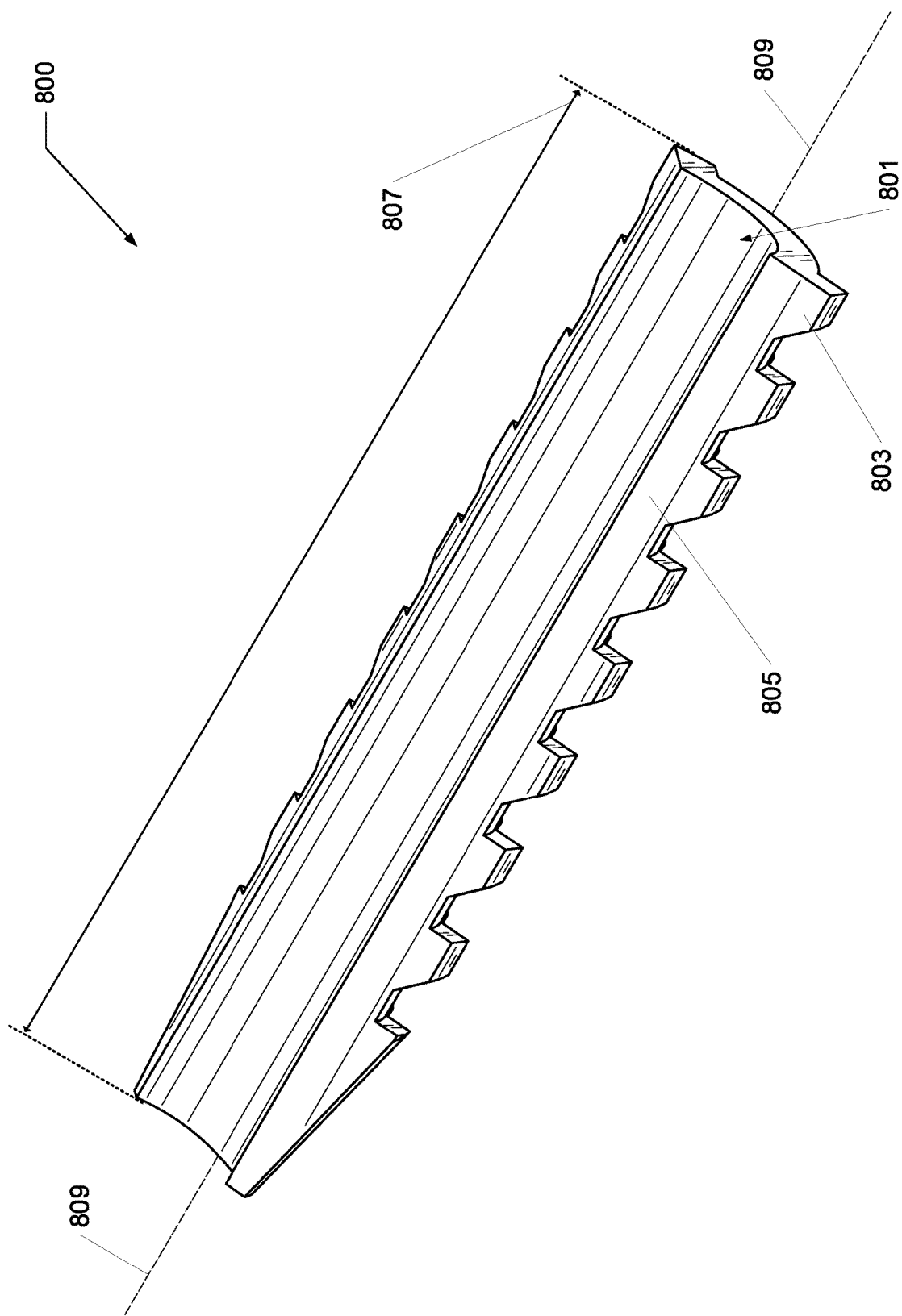
FIG. 8 is a perspective view of an exemplary pedicle insulator, according to one embodiment.

FIG. 8 illustrates a pedicle insulator 800. In one or more embodiments, the pedicle insulator 800 includes a channel 801. In at least one embodiment, the channel 801 may present a specific opening angle, such as one or more opening angles further illustrated in FIGS. 10 and 11.

In at least one embodiment, the pedicle insulator 800 includes a medial axis 809. In one or more embodiments, the medial axis is orthogonal to a proximate face of the pedicle insulator 800 (e.g., such as the proximate face 603 illustrated in FIG. 6). In various embodiments, the pedicle insulator 800 may be symmetrically bisected along the medial axis 809. In various embodiments, the channel 801 may be symmetrically oriented along the medial axis 809.

In at least one embodiment, the surface of the channel 801 may be smooth and may include a semi-circular shape. In one or more embodiments, the channel 801 presents a geometry that conforms to a generally cylindrical geometry of a pedicle screw. The channel 801, presenting a smooth surface and a conformational geometry may precisely and accurately direct insertion of a pedicle screw to a target implantation site without disrupting pedicle screw insertion or increasing pedicle screw insertion force. In at least one embodiment, the channel 801 may prevent damage by the pedicle screw (e.g., due to edges of the screw and/or a screw tip) to surrounding tissue, because the channel 801 may precisely and accurately direct insertion of the pedicle screw to the target implantation site.

In various embodiments, the pedicle insulator 800 may include one or more inner channelization surfaces 803 included on an exemplary tooth, such as the tooth 613 of FIG. 6. In one or more embodiments, the inner channelization surface 803 may be oriented parallel to an outer channelization surface, such as the outer channelization tooth surface 621 of FIG. 6. In at least one embodiment, the inner channelization surface may be oriented parallel to the insertion direction of the exemplary pedicle insulator. In various embodiments, the pedicle insulator 800 may include a number of inner channelization surfaces 803 equal to a number of teeth included on the pedicle insulator 600, each illustrated in FIG. 6.

In one or more embodiments, the pedicle insulator 800 may include a runner 805. In various embodiments, the pedicle insulator 800 may include two runners. In at least one embodiment, the runner 805 may diffuse biomechanical and other stresses experienced by one or more sections of the exemplary pedicle insulator; in particular, the runner 805 may diffuse stresses experienced by teeth included in the exemplary pedicle insulator. In various embodiments, the runner 805 may be located adjacent to the channel 801 and may be oriented parallel to the medial axis 809.

In one or more embodiments, the pedicle insulator 800 may include a length 807, wherein the length 807 refers to an overall length of the exemplary pedicle insulator. In various embodiments, the pedicle insulator length 807 may be standardized across iterations of the pedicle insulator and/or may be determined on a case by case basis. In at least one embodiment, the pedicle insulator length 807 may be between about 15 mm and about 50 mm. In at least one embodiment the pedicle insulator length 807 may measure between about 10-15 mm, between about 15-20 mm, between about 20-25 mm, between about 25-30 mm, between about 30-35 mm, between about 35-40 mm, between about 40-45 mm, between about 45-50 mm, or between about 50-55 mm.

Figure 9:
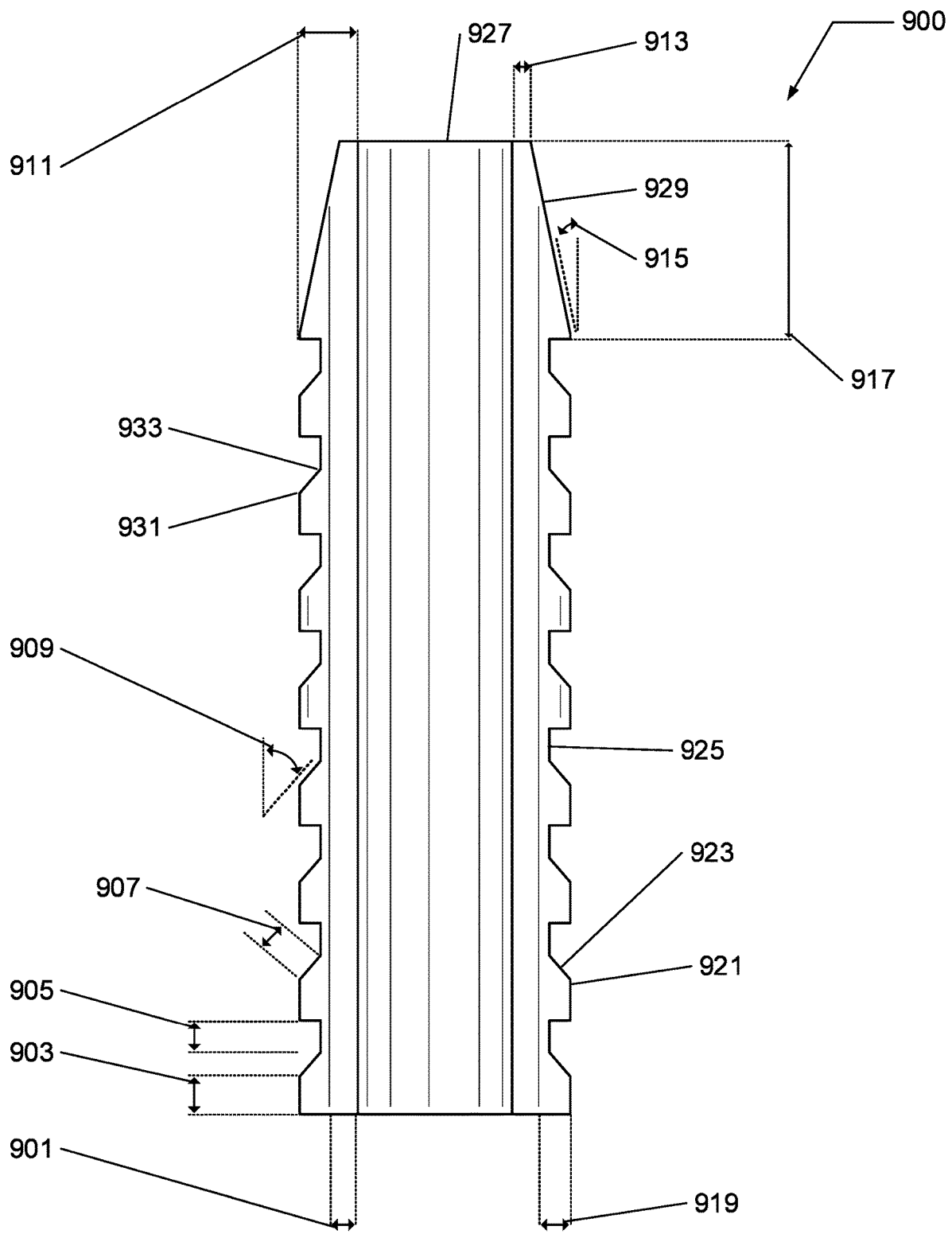
FIG. 9 is a back view of an exemplary pedicle insulator, according to one embodiment.

FIG. 9 illustrates a pedicle insulator 900. In various embodiments, the pedicle insulator 900 includes a runner thickness 901. In one or more embodiments, the runner thickness 901 may refer to a thickness of the runner 805 illustrated in FIG. 8. In at least one embodiment, the runner thickness 901 may contribute to the diffusion of biomechanical and or other stresses experienced by one or more teeth located on a runner. In one or more embodiments, the runner thickness 901 may be between about 0.5 mm and about 5 mm. In at least one embodiment the runner thickness 901 may measure between about 0.01-0.5 mm, between about 0.5-1.0 mm, between about 1.0-1.5 mm, between about 1.5-2.0 mm, between about 2.0-2.5 mm, between about 3.0-3.5 mm, between about 3.5-4.0 mm, between about 4.5-5.0 mm, between about 5.0-5.5 mm, or between about 5.5-6.0 mm.

In at least one embodiment, the pedicle insulator 900 may include a tooth outer surface 921, a tooth taper surface 923, a tooth gap 925, a tip 927 and a tapered tip surface 929. In one or more embodiments, the dimensions, properties, geometries and orientations of the tooth outer surface 921, the tooth taper surface 923, the gap 925, the tip 927 and the tapered tip surface 929 may be substantially similar to like features described herein in reference to other drawing figures.

In various embodiments, the pedicle insulator 900 includes a tooth body length 903. In one or more embodiments, the tooth body length 903 may generally refer to a length of the tooth outer surface 921. In at least one embodiment, the tooth body length 903 does not include the length of the tooth tapered surface 923. In some embodiments, the tooth body length 903 may be between about 0.1 mm and about 3 mm. In at least one embodiment the tooth body length 903 may measure between about 0.01-0.1 mm, between about 0.1-0.3 mm, between about 0.3-0.5 mm, between about 0.5-0.7 mm, between about 0.7-0.9 mm, between about 0.9-1.1 mm, between about 1.1-1.3 mm, between about 1.3-1.5 mm, between about 1.5-1.7 mm, between about 1.7-1.9 mm, between about 1.9-2.1 mm, between about 2.1-2.3 mm, between about 2.3-2.5 mm, between about 2.5-2.7 mm, between about 2.7-2.9 mm, between about 2.9-3.1 mm, or between about 3.1-3.3 mm.

In various embodiments, the pedicle insulator 900 includes a tooth gap length 905. In one or more embodiments, the tooth gap length 905 may generally refer to a length of the gap 925. In at least one embodiment, the tooth gap length does not include the length of the tooth tapered surface 923. In some embodiments, the tooth gap length 905 may be between about 0.1 mm and about 3 mm. In at least one embodiment the tooth gap length 905 may measure between about 0.01-0.1 mm, between about 0.1-0.3 mm, between about 0.3-0.5 mm, between about 0.5-0.7 mm, between about 0.7-0.9 mm, between about 0.9-1.1 mm, between about 1.1-1.3 mm, between about 1.3-1.5 mm, between about 1.5-1.7 mm, between about 1.7-1.9 mm, between about 1.9-2.1 mm, between about 2.1-2.3 mm, between about 2.3-2.5 mm, between about 2.5-2.7 mm, between about 2.7-2.9 mm, between about 2.9-3.1 mm, or between about 3.1-3.3 mm.

In various embodiments, the pedicle insulator 900 includes a tooth tapered surface length 907. In one or more embodiments, the tooth tapered surface length 907 may refer to a length (e.g., oriented as illustrated in FIG. 9) between an initiating taper point 931 and a terminating taper point 933 of the tooth tapered surface 923. In some embodiments, the tooth tapered surface length 907 may be between about 0.1 mm and about 2 mm. In at least one embodiment the tooth tapered surface length 907 may measure between about 0.01-0.1 mm, between about 0.1-0.3 mm, between about 0.3-0.5 mm, between about 0.5-0.7 mm, between about 0.7-0.9 mm, between about 0.9-1.1 mm, between about 1.1-1.3 mm, between about 1.3-1.5 mm, between about 1.5-1.7 mm, between about 1.7-1.9 mm, between about 1.9-2.1 mm, or between about 2.1-2.3 mm.

In various embodiments, the pedicle insulator 900 includes a tooth taper angle 909. In one or more embodiments, the tooth taper angle 909 may generally refer to an exterior angle between the tooth outer surface 921 and the tooth tapered surface 923. In at least one embodiment, the tooth taper angle 909 may be between about 5° and about 45°.

In various embodiments, the pedicle insulator 900 may include a tip wall initial thickness 911. In one or more embodiments, the tip wall initial thickness 911 may include the sum of the runner thickness 901 and a height of a tooth (e.g., as described further herein). In at least one embodiment, the tip wall initial thickness 911 may refer to a thickness of the curved wall (not illustrated in FIG. 9) of the tip 927 prior to tapering. In various embodiments, the tip wall initial thickness 911 may be greater than the runner thickness 901. In one or more embodiments, the tip wall initial thickness 911 may be between about 0.5 mm and about 5 mm. In at least one embodiment the tip wall initial thickness 911 may measure between about 0.01-0.5 mm, between about 0.5-1.0 mm, between about 1.0-1.5 mm, between about 1.5-2.0 mm, between about 2.0-2.5 mm, between about 3.0-3.5 mm, between about 3.5-4.0 mm, between about 4.5-5.0 mm, between about 5.0-5.5 mm, or between about 5.5-6.0 mm.

In various embodiments, the pedicle insulator 900 may include a tip wall terminal thickness 913. In one or more embodiments, the tip wall terminal thickness 913 may refer to a thickness of the curved wall (not illustrated in FIG. 9) of the tip 927 at the conclusion of tapering. In various embodiments, the tip wall terminal thickness 913 may be less than the runner thickness 901 and may be less than the height of one tooth. In one or more embodiments, the tip wall terminal thickness 913 may be between about 0.5 mm and about 5 mm. In at least one embodiment the tip wall terminal thickness 913 may measure between about 0.01-0.5 mm, between about 0.5-1.0 mm, between about 1.0-1.5 mm, between about 1.5-2.0 mm, between about 2.0-2.5 mm, between about 3.0-3.5 mm, between about 3.5-4.0 mm, between about 4.5-5.0 mm, between about 5.0-5.5 mm, or between about 5.5-6.0 mm.

In various embodiments, the pedicle insulator 900 may include a tip taper angle 915. In one or more embodiments, the tip taper angle 915 may refer to an exterior angle between one of the outer tooth surface 921 and one of the tapered tip surface 929. In at least one embodiment, the tip taper angle 915 may be between about 5° and about 45°. In one or more embodiments, the tip taper angle may be less than the tooth taper angle 909.

In various embodiments, the pedicle insulator 900 may include a tip length 917. In one or more embodiments, the tip length 917 may refer to a length of the tip 927. In at least one embodiment, the tip length 917 may be between about 1 mm and about 15 mm. In at least one embodiment the tip length 917 may measure between about 0.01-2.0 mm, between about 2.0-4.0 mm, between about 4.0-6.0 mm, between about 6.0-8.0 mm, between about 8.0-10.0 mm, between about 10.0-12.0 mm, between about 12.0-14.0 mm, or between about 14.0-16.0 mm.

In various embodiments, the pedicle insulator 900 may include a tooth height 919. In one or more embodiments, the tooth height 919 may refer to a height of a tooth (e.g., as described elsewhere herein). In at least one embodiment, the tooth height 919 may be between about 0.5 mm and about 5 mm. In at least one embodiment the tooth height 919 may measure between about 0.01-0.5 mm, between about 0.5-1.0 mm, between about 1.0-1.5 mm, between about 1.5-2.0 mm, between about 2.0-2.5 mm, between about 3.0-3.5 mm, between about 3.5-4.0 mm, between about 4.5-5.0 mm, between about 5.0-5.5 mm, or between about 5.5-6.0 mm. In various embodiments, the tooth height 919 may be equal to a height of a pedicle screw thread.

Figure 10:
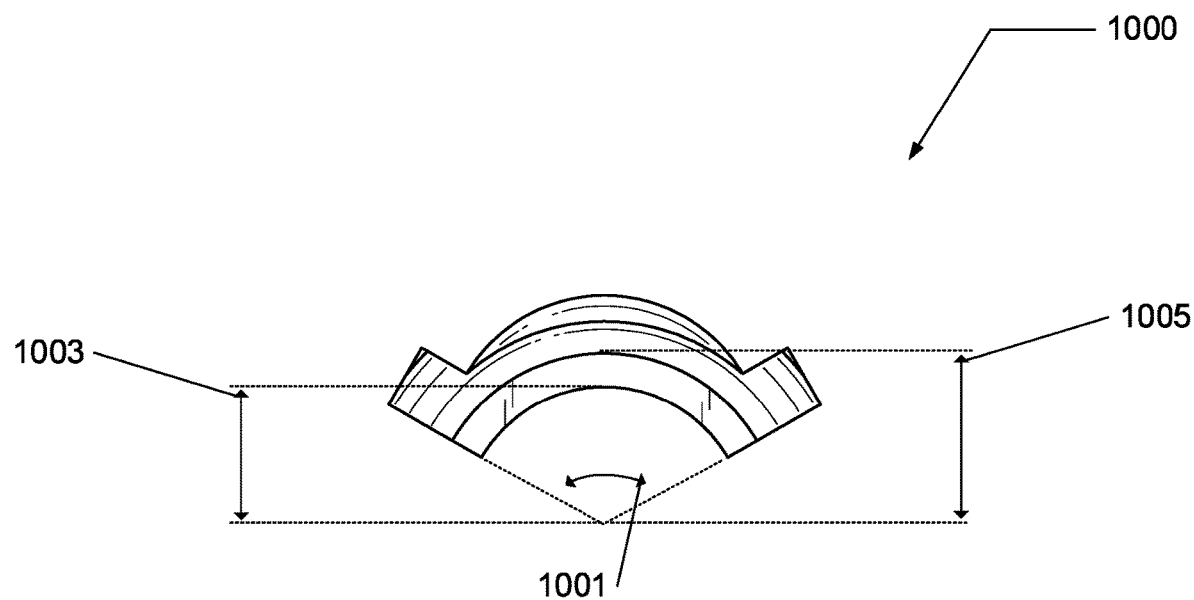
FIG. 10 is a bottom view of an exemplary pedicle insulator, according to one embodiment.

FIG. 10 illustrates a pedicle insulator 1000. In various embodiments, the pedicle insulator 1000 includes an opening angle 1001. In one or more embodiments, a magnitude of the opening angle 1001 may be about 120°, about 180°, or one or more other magnitudes. In at least one embodiment, the magnitude of the opening angle 1001 may be determined, in part, by a geometry of an associated pedicle screw, a geometry of an associated insertion area (e.g., a pedicle insertion hole), and/or other geometric factors.

In various embodiments, the pedicle insulator 1000 includes an inner radius 1003. In one or more embodiments, a magnitude of the inner radius 1003 may be about 2.25 mm, about 2.75 mm, about 3.25 mm, about 3.5 mm, or one or more other magnitudes. In at least one embodiment the inner radius 1003 may measure between about 1.75-2.0 mm, between about 2.0-2.25 mm, between about 2.25-2.50 mm, between about 2.5-2.75 mm, between about 2.75-3.0 mm, between about 3.0-3.25 mm, between about 3.25-3.5 mm, between about 3.5-3.75 mm, between about 3.75-4.0 mm, or between about 4.0-4.25 mm. In at least one embodiment, the magnitude of the inner radius 1003 may be determined, in part, by a geometry of an associated pedicle screw, a geometry of an associated insertion area (e.g., a pedicle insertion hole), and/or other geometric factors.

In various embodiments, the pedicle insulator 1000 includes an outer radius 1005. In one or more embodiments, a magnitude of the outer radius 1005 may be about 2.5 mm, or one or more other magnitudes. In at least one embodiment the outer radius 1005 may measure between about 1.75-2.0 mm, between about 2.0-2.25 mm, between about 2.25-2.50 mm, between about 2.5-2.75 mm, between about 2.75-3.0 mm, between about 3.0-3.25 mm, between about 3.25-3.5 mm, between about 3.5-3.75 mm, between about 3.75-4.0 mm, between about 4.0-4.25 mm, between about 4.25-4.5 mm, between about 4.5-4.75 mm, or between about 4.75-5.0 mm. In at least one embodiment, the magnitude of the outer radius 1005 may be determined by a combination of one or more other measurement factors including, but not limited to: 1) the opening angle 1001; 2) the inner radius 1003; and 3) a tip terminal wall thickness, such as the tip terminal wall thickness 913 of FIG. 9.

Figure 11:
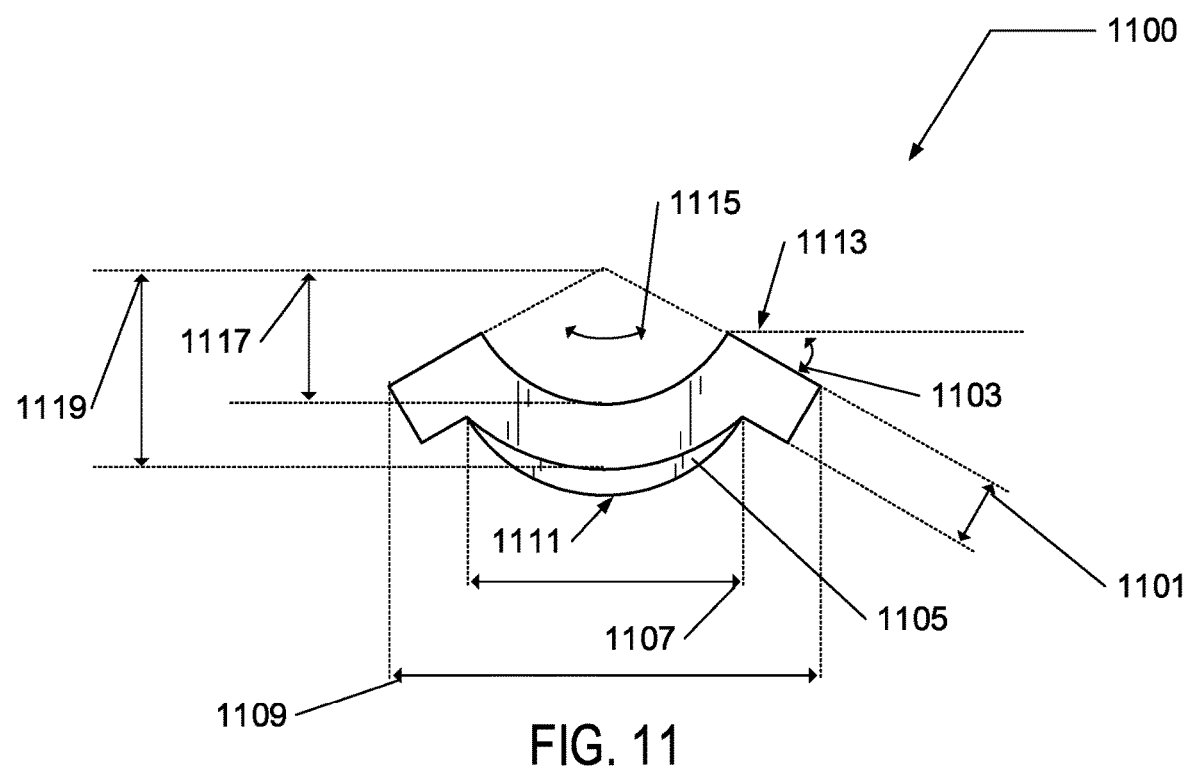
FIG. 11 is a top view of an exemplary pedicle insulator, according to one embodiment.

FIG. 11 illustrates a pedicle insulator 1100. In at least one embodiment, the pedicle insulator 1100 may include a ridge 1111, a runner 1113, an opening angle 1115, an inner radius 1117 and an outer radius 1119. In one or more embodiments, the dimensions, properties, geometries and orientations of the ridge 1111, the runner 1115, the opening angle 1115 and the inner radius 1117 may be substantially similar to similar features described herein. In at least one embodiment, a magnitude of the outer radius 1119 may be about 2.5 mm. In at least one embodiment the outer radius 1119 may measure between about 1.75-2.0 mm, between about 2.0-2.25 mm, between about 2.25-2.50 mm, between about 2.5-2.75 mm, between about 2.75-3.0 mm, between about 3.0-3.25 mm, between about 3.25-3.5 mm, between about 3.5-3.75 mm, between about 3.75-4.0 mm, between about 4.0-4.25 mm, between about 4.25-4.5 mm, between about 4.5-4.75 mm, or between about 4.75-5.0 mm. In some embodiments, the magnitude of the outer radius 1119 may be determined by a combination of one or more other measurement factors including, but not limited to: 1) the opening angle 1115; and 2) the inner radius 1117.

In various embodiments, the pedicle insulator 1100 includes a runner height 1101. In one or more embodiments, the runner height 1101 may describe a height of the runner 1113 and may also describe a width of a tooth (e.g., as described elsewhere herein). In at least one embodiment, a magnitude of the runner height 1101 may be between about 0.5 mm and about 5 mm. In at least one embodiment the runner height 1101 may measure between about 0.01-0.5 mm, between about 0.5-1.0 mm, between about 1.0-1.5 mm, between about 1.5-2.0 mm, between about 2.0-2.5 mm, between about 3.0-3.5 mm, between about 3.5-4.0 mm, between about 4.5-5.0 mm, between about 5.0-5.5 mm, or between about 5.5-6.0 mm. In some embodiments, the magnitude of the runner height 1101 may be dependent, in part, upon the respective magnitudes of the inner radius 1117 and outer radius 1119.

In various embodiments, the pedicle insulator 1100 includes a runner angle 1103. In one or more embodiments, the runner angle 1103 may refer to the angle between a surface of the runner 1113 and a horizontal plane, wherein the exemplary pedicle insulator of the pedicle insulator 1100 lies immediately beneath the plane. In at least one embodiment, a magnitude of the runner angle 1103 may be between about 0° and about 60°. In one or more embodiments, the magnitude of the runner angle 1103 may be selected such that the runner height 1101 is greater than 0 mm.

In various embodiments, the pedicle insulator 1100 includes a ridge fixation surface 1105. In one or more embodiments, the ridge fixation surface 1105 may be a fixation surface of the ridge 1111. In at least one embodiment, the ridge fixation surface 1105 may be oriented orthogonal to the insertion direction of a pedicle insulator. In various embodiments, the orientation of the ridge fixation surface 1105 increases manner the magnitude of a pullout force (e.g., in a direction parallel and opposite to the insertion direction) required to remove the exemplary pedicle insulator.

In various embodiments, the pedicle insulator 1100 includes a ridge width 1107. In one or more embodiments, the ridge width 1107 may refer to a width of the ridge 1111. In at least one embodiment, a magnitude of the width 1107 may be about 2.3 mm, about 4.5 mm, about 5.3 mm, about 6.2 mm, about 6.5 mm, or one or more other magnitudes. In at least one embodiment the ridge width 1107 may measure between about 1.0-1.5 mm, between about 1.5-2.0 mm, between about 2.0-2.5 mm, between about 2.5-3.0 mm, between about 3.0-3.5 mm, between about 3.5-4.0 mm, between about 4.0-4.5 mm, between about 4.5-5.0 mm, between about 5.5-6.0 mm, between about 6.0-6.5, between about 6.5-7.0, or between about 7.0-7.5 mm.

In various embodiments, the pedicle insulator 1100 includes a pedicle insulator width 1109. In one or more embodiments, a magnitude of the pedicle insulator width 1109 may be determined by a combination of one or more other measurement factors including, but not limited to: 1) the opening angle 1115; 2) the inner radius 1117; and 3) the ridge width 1119. In at least one embodiment, the magnitude of the pedicle insulator width 1109 may be about 4.9 mm, about 7.9 mm, about 8.3 mm, about 9.7 mm, or one or more other magnitudes.

Figure 12:
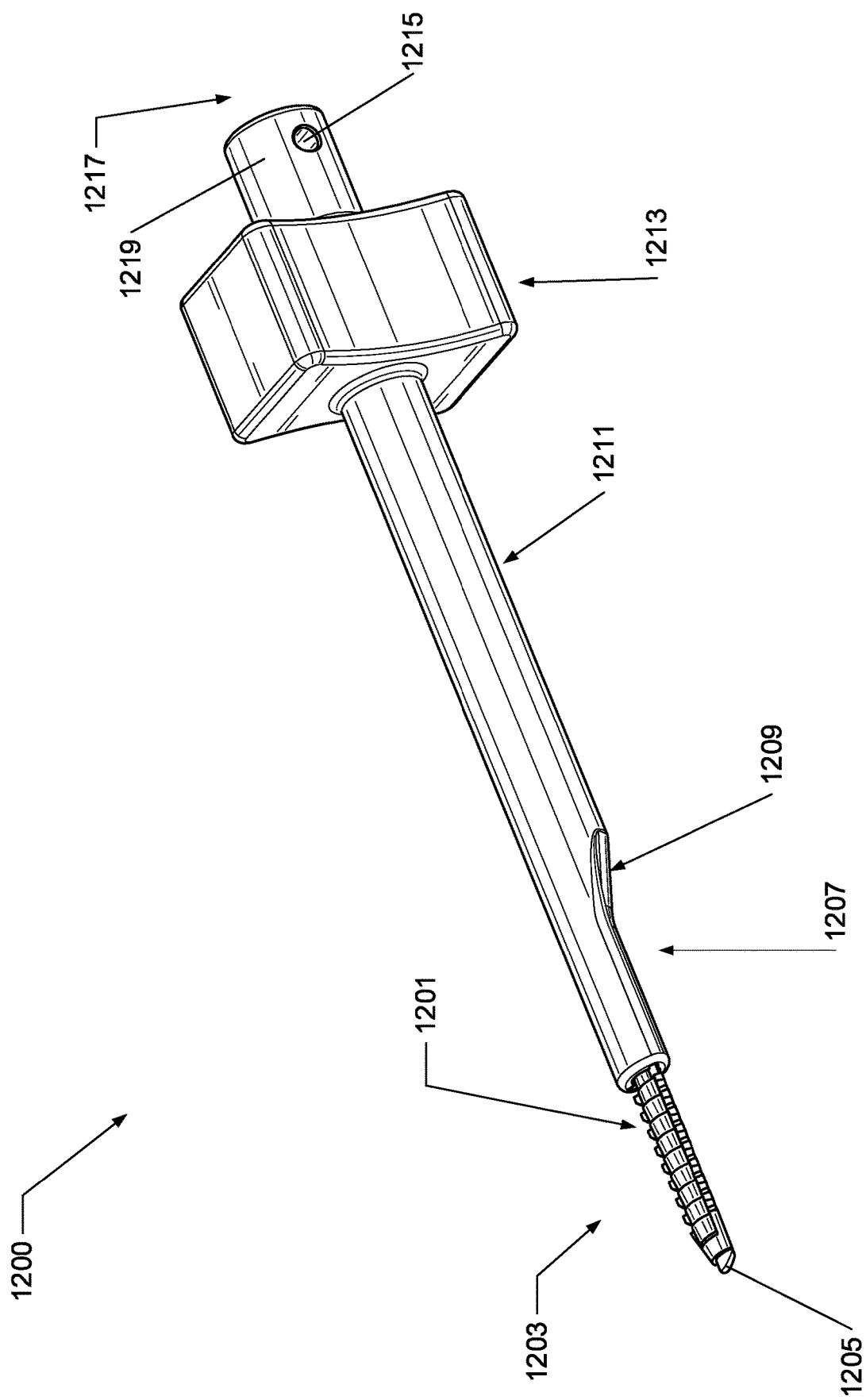
FIG. 12 is a perspective view of an exemplary pedicle insulator inserter with pedicle insulator, according to one embodiment.

FIG. 12 illustrates a pedicle insulator inserter 1200, referred to herein as an "inserter." In various embodiments, an inserter provides a mechanism for deploying a pedicle insulator 1201 to a target site (e.g., on or within a body). In at least one embodiment, the inserter 1200 may deploy the pedicle insulator 1201 from a distal end 1203. In one or more embodiments, the inserter 1200 includes a guide rod 1205, wherein the pedicle insulator 1201, prior to and during deployment, rests along the guide rod 1205. Thus, the guide rod 1205 may include a relatively cylindrical geometry, wherein a diameter of the relatively cylindrical geometry may be based on an outer radius of the pedicle insulator 1201. In some embodiments, the guide rod 1205 may include materials including, but not limited to, stainless steel, or one or more other materials suitable for use in a surgical environment. In at least one embodiment, the guide rod 1205 may include a rod length (not illustrated) that may be substantial similar to a length of the inserter 1200.

Figure 14:
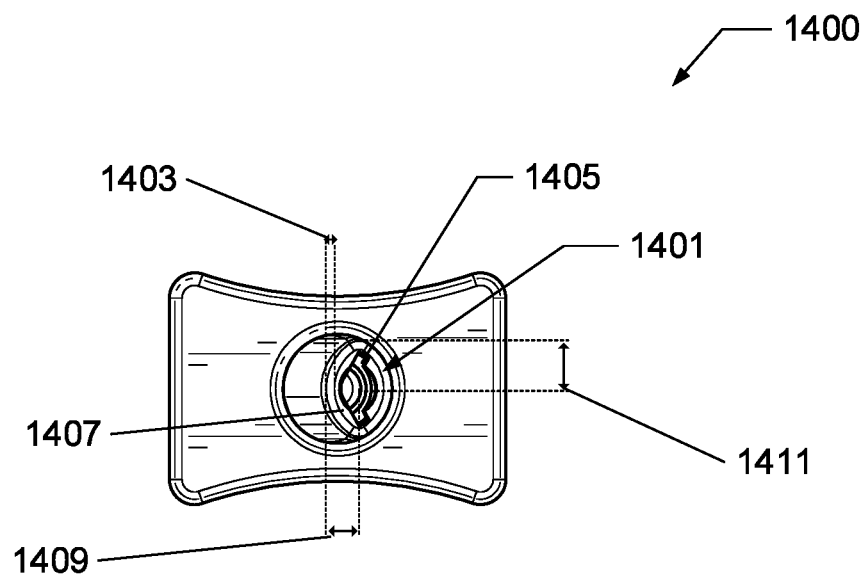
FIG. 14 is a bottom view of an exemplary pedicle insulator inserter with pedicle insulator, according to one embodiment.
Figure 15:
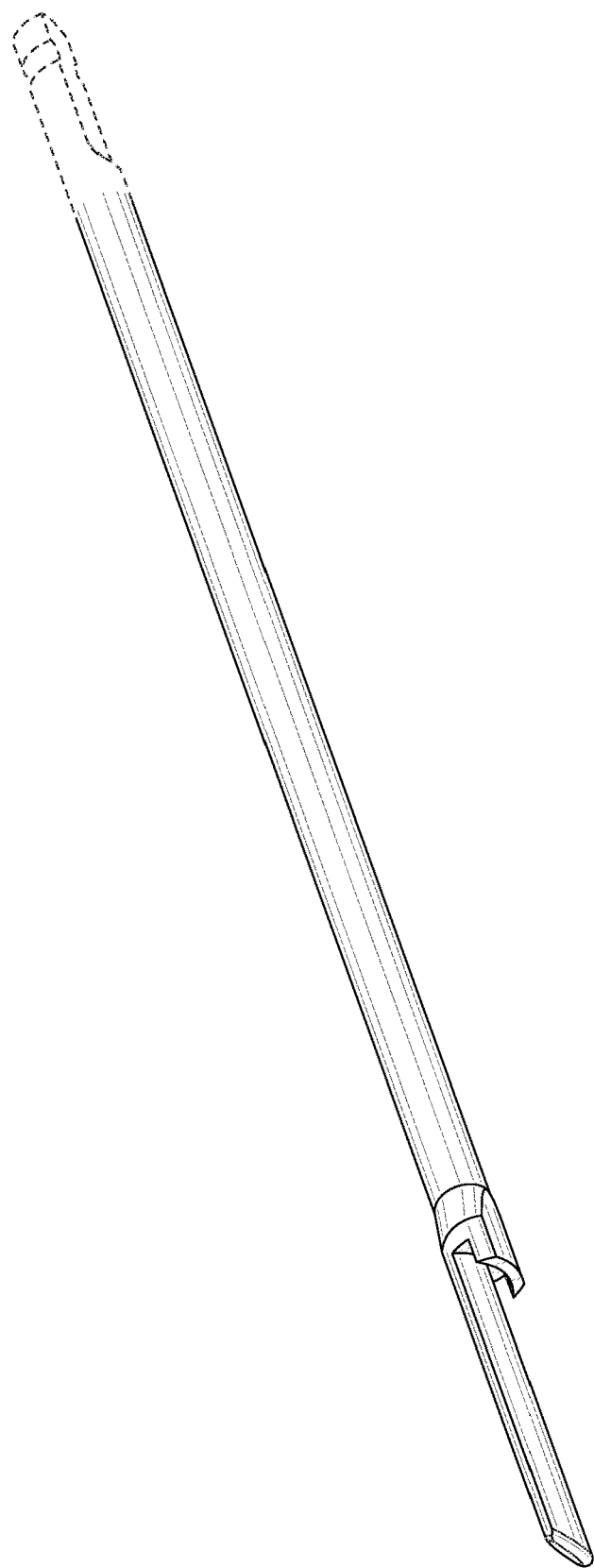
FIG. 15 is a perspective view of an exemplary pedicle insulator inserter, according to one embodiment.
Figure 16:
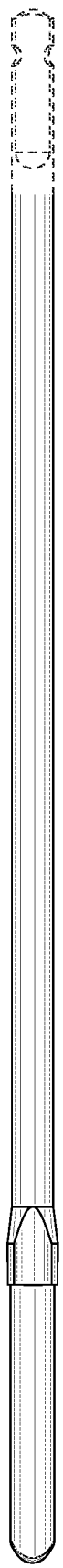
FIG. 16 is a front view of an exemplary pedicle insulator inserter, according to one embodiment.
Figure 17:
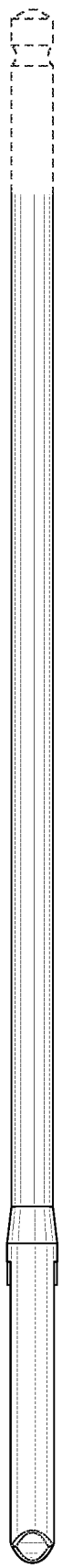
FIG. 17 is a back view of an exemplary pedicle insulator inserter, according to one embodiment.
Figure 18:
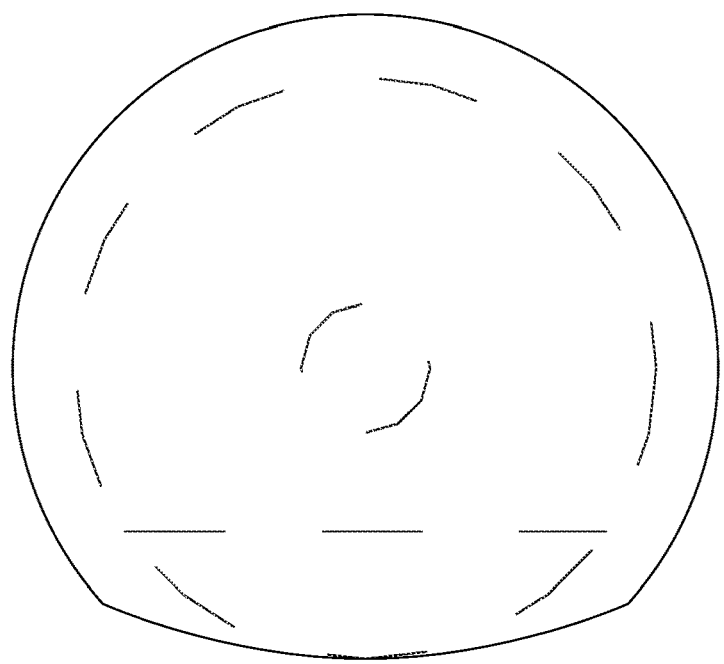
FIG. 18 is a top view of an exemplary pedicle insulator inserter, according to one embodiment.
Figure 19:
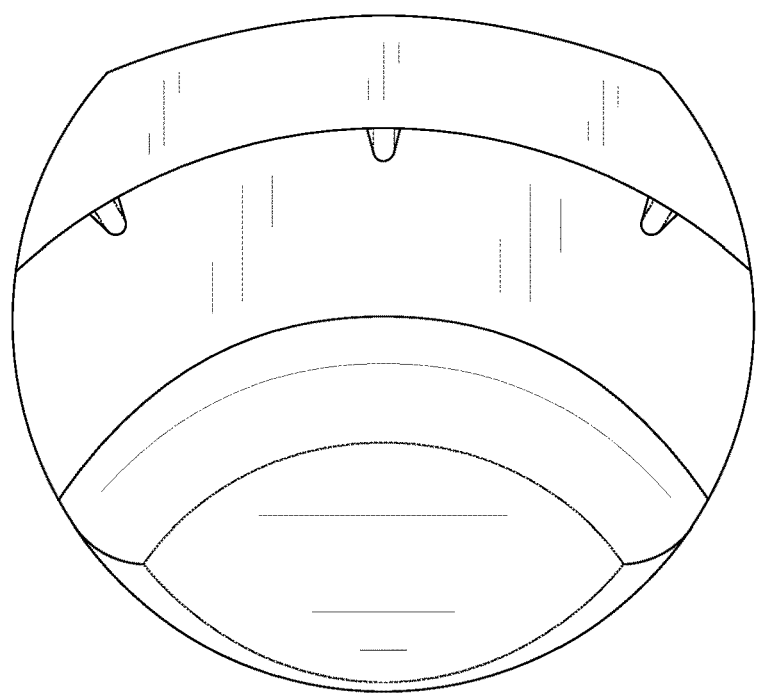
FIG. 19 is a bottom view of an exemplary pedicle insulator inserter, according to one embodiment.
Figure 20:
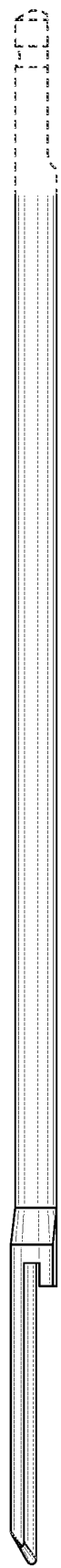
FIG. 20 is a side view of an exemplary pedicle insulator inserter, according to one embodiment.
Figure 21:
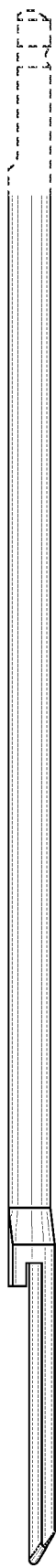
FIG. 21 is a side view of an exemplary pedicle insulator inserter, according to one embodiment.

Continuing with FIG. 12, in various embodiments, the inserter 1200 includes a first shaft section 1207. In at least one embodiment, the first shaft section 1207 includes an elliptical cross section. Thus, (as illustrated in FIG. 14 and further described herein) the cross section of the first shaft section 1207 may present a semi-major axis and a semi-minor axis (e.g., that is of lesser magnitude than the semi-major axis). One of ordinary skill in the art will understand that a semi-major axis is a longest diameter of an ellipse, thus the semi-major axis is a line segment that runs through the center and both foci of an ellipse. One of ordinary skill in the art will further understand that a semi-minor axis refers to a diameter that is orthogonal to the semi-major axis and also runs through the center of the ellipse. In some embodiments, the first shaft section 1207 may be integrally formed with one or more components of the inserter 1200. In at least one embodiment, when the inserter 1200 is in a non-deployed state, the insulator 1201 may be substantially recessed within the first shaft section 1207.

In one or more embodiments, the inserter 1200 includes a second shaft section 1211. In at least one embodiment, the second shaft section 1211 includes a substantially circular cross section. In some embodiments, the second shaft section 1211 may be integrally formed with one or more components of the inserter 1200. In various embodiments (as described further herein), the circular cross section of the second shaft section 1211 may present a diameter that is equal in length to the semi-major axis of the first shaft section 1207. In at least one embodiment, in a non-deployed state, the second shaft section 1211 may partially contain the pedicle insulator 1201 and may substantially contain the guide rod 1205. As illustrated in FIG. 12, in a deployed state, the second shaft section 1211 may substantially contain the guide rod 1205.

In at least one embodiment, the pedicle inserter 1200 includes a shaft taper section 1209 that is disposed between the first shaft section 1207 and the second shaft section 1211. In one or more embodiments, the taper section 1209 initially presents (e.g., towards the proximate end 1217) a substantially circular cross section that is congruent to the circular cross section of the second shaft section 1211. In at least one embodiment, the taper section 1209 presents (e.g., towards the distal end 1203) a substantially elliptical cross section that is congruent to the elliptical cross section of the first shaft section 1207.

In various embodiments, the taper section 1209 tapers (from circular to elliptical) as the section progresses toward the distal end 1203. Thus, towards the proximate end 1217, the taper section 1209 may present a circular cross section (e.g., with a single diameter) and, towards the distal end 1203, may present an elliptical cross section. As illustrated in FIG. 12, the initial circular cross section, having a single diameter, may smoothly deform (e.g., taper) into an elliptical cross section, having a semi-major axis and a semi-minor axis. Thus, in various embodiments, the shaft taper section 1209 may function as a geometric transition zone between the first shaft section 1207 and the second shaft section 1211.

In various embodiments, the inserter 1200 includes a handle 1213. In at least one embodiment, the handle 1213 (e.g., as illustrated in FIG. 12) may be disposed between the second shaft section 1211 and a proximate end 1217. In one or more embodiments, the handle 1213 may include a mostly rectangular prismatic geometry, and may further include (e.g., as described later herein) one or more features, which may improve a user's ability to grip and/or otherwise interact with the handle 1213. In at least one embodiment, the handle 1213 may be designed in a manner such that a user can precisely and accurately orient the inserter 1200 to a target site.

In some embodiments, the inserter 1200 may include a strike plate 1219 located near the proximate end 1217. In one or more embodiments, the strike plate 1219 may present a substantially flat top surface (not illustrated in FIG. 12) that is configured to receive a striking force (e.g., from a mallet or the like) and transfer the force into translational movement of the guide rod 1205 and pedicle insulator 1201 through the first shaft 1211 and second shaft 1207 and out the distal end 1203 of the inserter 1200. In various embodiments, the strike plate 1219 forms or defines a pin-hole 1215 that may function as a component in a grenade-pin configuration which may prevent deployment of the inserter 1200 and insulator 1201. Thus, when a pin (not illustrated) is inserted into the pin-hole 1215 (e.g., while the strike-plate 1219 is drawn upwards from the inserter 1200), movement of the strike plate 1219 may be restricted.

As shown FIG. 12, the inserter 1200 is in a deployed state. In various embodiments, in the deployed state, the pin-hole 1215 may be devoid of a pin (e.g., as illustrated in FIG. 12) and the strike plate 1219 may be depressed towards the distal end 1203 and handle 1213. In at least one embodiment, in the deployed state, the guide rod 1205 may be partially disposed from the distal end 1205 and the pedicle insulator 1203 may be substantially or fully disposed from the distal end 1205 (e.g., as a result of strike plate position).

In one or more embodiments, in a non-deployed state, the inserter 1200 may house the pedicle insulator 1201 and a substantial length of the guide rod 1205 within the first shaft section 1207 and the second shaft section 1211. In at least one embodiment, in the non-deployed state, the strike plate 1219 may be drawn upwards from the inserter 1200 and towards the proximate end 1217. Thus, the guide rod 1205 and pedicle insulator 1201 may be recessed within the inserter 1200 as a result of the strike plate 1219 being drawn upwards. In at least one embodiment, in the non-deployed state, a pin is placed within the pin-hole 1215, thus restricting movement of the strike plate 1215.

Deployment of the pedicle insulator 1201 from the inserter 1200 to a target site may include, but is not limited to: 1) loading the pedicle insulator 1201 onto the guide rod 1205; 2) withdrawing the guide rod 1205 and pedicle insulator 1201 into the inserter 1200; 3) placing a pin into the pin hole 1215; 4) upon being required in a surgery, orienting the inserter; 5) removing the pin from the pin hole 1215; and 6) striking a strike plate, thereby deploying the pedicle insulator 1205 into a patient.

Figure 13:
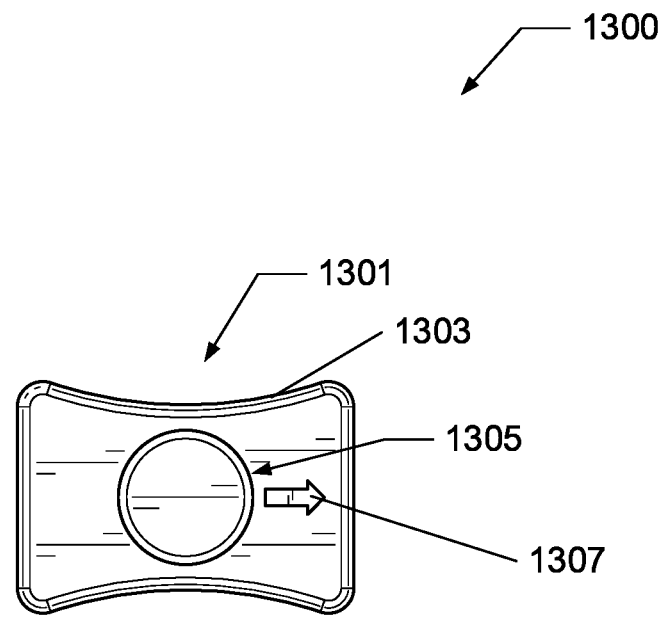
FIG. 13 is a top view of an exemplary pedicle insulator inserter, according to one embodiment.

FIG. 13 illustrates a pedicle insulator inserter 1300. In various embodiments, the inserter 1300 includes a handle 1301 and a strike plate 1305. In at least one embodiment, the strike plate 1305 may function as a target site for one or more striking motions, which may deploy a pedicle insulator from the inserter 1300. In one or more embodiments, the strike plate 1305 may include a grenade-pin mechanism, including a pin hole (e.g., for example, as is illustrated in FIG. 12) and a pin (not illustrated herein), for preventing accidental deployment. In some embodiments, the handle 1301 may include at least one curved edge 1303 providing an ergonomic gripping and/or handling surface.

In various embodiments, the handle 1301 may include at least one orientation indicator 1307. In one or more embodiments, the indicator 1307 may include a raised, impressed, or otherwise permanent demarcation containing textual and/or symbolic information relating to operation of the inserter 1300 (e.g., an arrow). In at least one embodiment, the indicator 1307 may present information indicating directionality of a pedicle insulator loaded within the inserter 1300.

FIG. 14 illustrates a pedicle insulator inserter 1400. In various embodiments, the inserter 1400 includes a first shaft section 1401. In one or more embodiments, the first shaft section 1401 may include a wall thickness 1403, which may be sized based on one or more dimensions of a pedicle insulator 1405 (e.g., as illustrated in FIG. 14 within the first shaft section 1401). In at least one embodiment, the first shaft section 1401 may include a baseplate 1407, wherein the base plate 1407 may be disposed at the end of the first shaft section 1401. In some embodiments, the base plate 1407 may include an elliptical shape, wherein a profile of the pedicle insulator 1405 and a guide rod are carved through the baseplate 1407. Thus, the pedicle insulator 1405 and a guide rod may pass through the baseplate 1407 (e.g., upon deployment of the pedicle insulator as described above, or otherwise).

In at least one embodiment, the first shaft section 1401 may include an elliptical cross section. One of ordinary skill in the art will understand that dimensions of an elliptical cross section may be defined by a length of the elliptical cross section's semi-minor and semi-major axes. One of ordinary skill in the art will further understand that: 1) the semi-major axis refers to a longest diameter of an ellipse (e.g., the elliptical cross section) that is a line segment that runs from the center of the ellipse to a perimeter of the ellipse (e.g., at a widest point of the ellipse); 2) the semi-minor axis refers to a line segment that runs from the center of the ellipse and is orthogonal to the semi-major axis. Thus, in various embodiments, the first shaft section 1401 includes a semi-minor axis length 1409 and a semi-major axis length 1411. In one or more embodiments, the semi-minor length 1409 and semi-major length 1411 may be dimensioned to accommodate passage of the pedicle insulator 1405 (e.g., during both loading into and deployment from the inserter 1400) through the baseplate 1407. Thus, the dimensions of the first shaft section 1401 may be sized in a manner such that the pedicle insulator 1405 may pass through an interior of the shaft section 1401 (e.g., both into and out of the inserter 1400).

FIGS. 15-21 illustrate an additional embodiment of a pedicle insulator inserter. As described in greater detail below, a pedicle insulator may be secured to the inserter and delivered into a target site (in particular, a void thereof).

Figure 22:
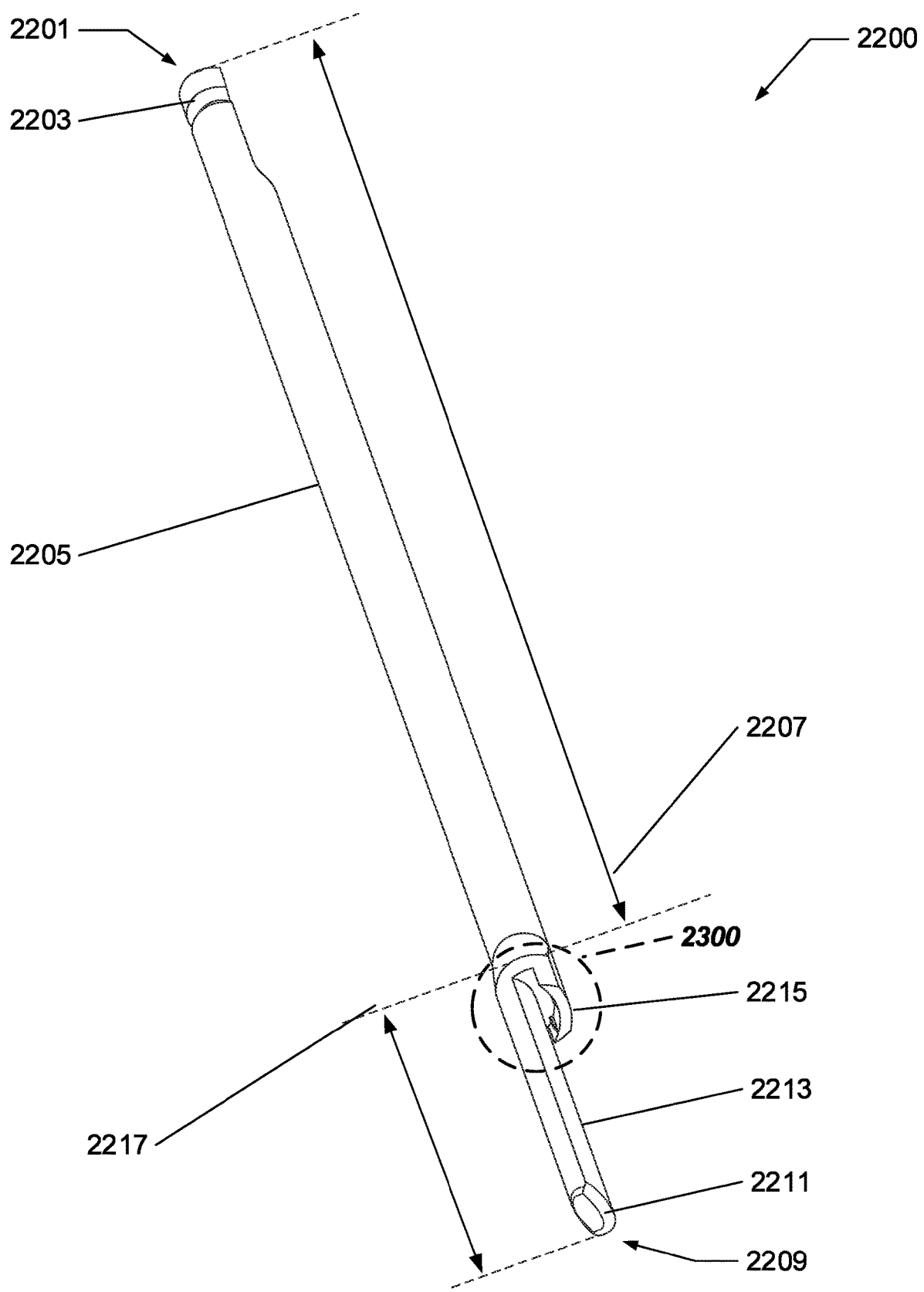
FIG. 22 is a perspective view of an exemplary pedicle insulator inserter, according to one embodiment.

FIG. 22 illustrates a pedicle insulator inserter 2200. In various embodiments, the inserter 2200 may be manufactured from materials including, but not limited to, stainless steel, or one or more other materials suitable for use in a surgical environment. In at least one embodiment, the inserter 2200 may be disposable or may be suitable for re-use following sterilization techniques such as autoclaving.

In various embodiments, the inserter 2200 includes a proximal end 2201. In one or more embodiments, the inserter 2200 further includes a connector 2203 located at the proximal end 2201. In at least one embodiment, the connector 2203 may be an attachment point for a quick-connect apparatus (for example, an AO quick-connect apparatus). Thus, the connector 2203 may facilitate simplified and rapid attachment of any apparatus (e.g., handles, etc.) that also include quick-connect attachment features.

In various embodiments, the inserter 2200 includes a primary shaft 2205, which is generally cylindrical in shape. In one or more embodiments, the primary shaft 2205 includes a primary shaft length 2207. In at least one embodiment, the primary shaft length 2207 may measure between about 50-300 mm or about 120-140 mm. In various embodiments, the primary shaft length 2207 may measure between about 50-100 mm, between about 100-150 mm, between about 150-200 mm, between about 200-250 mm, between about 250-300 mm, or between about 300-350 mm. In at least one embodiment, the primary shaft length 2207 may be selected to accommodate placement of a pedicle insulator (e.g., into a patient) and/or to accommodate a particular surgical approach to pedicle insulator placement. In one or more embodiments, the primary shaft length 2207 may be further selected to accommodate patient anatomy (e.g., dimensions thereof). For example, a particular patient may present a larger than average anatomy; accordingly, a primary shaft length 2207 may be selected to compensate for the larger anatomy (e.g., a longer primary shaft length 2207 may be selected).

In various embodiments, the inserter 2200 includes a distal end 2209 and a tip 2211 located near the distal end 2209. In one or more embodiments, the tip 2211 may be filleted. Per the present disclosure, filleted refers to geometric features of the tip 2211 that are substantially devoid of projecting edges and points, and present at least one curved surface. In one or more embodiments, the use of curved geometries and the minimization of projecting edges may reduce a capacity of the tip 2211 to puncture tissue (e.g., compared to a tip presenting straight and pointed geometries). Thus, the tip 2211 may be filleted in a manner such that a minimum magnitude of force required to puncture tissue is increased (compared to a minimum force required to puncture tissue using a non-filleted tip). In at least one embodiment, the tip 2211 may include edges that are chamfered, rounded or otherwise blunted in a manner such that a minimum magnitude of force required to lacerate tissue may be increased (e.g., compared to a minimum force required to lacerate tissue using a non-blunted tip).

In at least one embodiment, filleting of the tip 2211 may improve ease of orientation and insertion of the inserter 2200 into a target site. For example, a non-filleted tip (e.g., presenting a more substantially square-cross section) may be more likely, due to its angular geometry, to collide with an edge of a substantially circular target site. Thus, a more angular tip geometry may increase a likelihood that, upon orientation of the inserter, the tip will strike an edge of a target site. Furthermore, in the same example, because the non-filleted tip does not include filleted surfaces (e.g., that may bias the inserter towards placement into the target site), the filleted-tip may require further orientation before successful insertion into the target site can be achieved.

In contrast, in the same example, a filleted tip may be less likely to collide with an edge of the substantially circular target site, because the filleted tip presents a less angular geometry. Furthermore, if the filleted tip does come into contact with an edge of the target site, filleted surfaces of the tip may bias the inserter towards placement into the target site, because the filleted surfaces may be angled such that a path of least resistance is a path further into the target site. Thus, the tip 2211 may be filleted for purposes including, but not limited to: 1) reducing likelihood of an inserter striking an edge of a target site (e.g., in a manner that impedes further placement of the inserter); and 2) biasing an inserter such that a path of least resistance (e.g., from a perspective of the tip 2211) is further into a target site.

In one or more embodiments, the inserter 2200 includes a secondary shaft 2213. In at least one embodiment, the secondary shaft 2213 may be disposed between the tip 2209 and the primary shaft 2205. In some embodiments, the tip 2209 and the secondary shaft 2213 may be integrally formed. In one embodiment, the tip 2209, secondary shaft 2213 and primary shaft 2205 may be integrally formed. In various embodiments, the secondary shaft 2213 may include a recess 2215 (e.g., which is described further herein and further illustrated in FIG. 23). In one or more embodiments, the recess 2215 temporarily secures a pedicle insulator to the inserter 2200 via a press-fit interface. In at least one embodiment, the secondary shaft 2213 further includes a secondary shaft length 2217 that may measure between about 10-50 mm or 30-34 mm. In various embodiments, the secondary shaft length 2217 may measure between about 10-15 mm, between about 15-20 mm, between about 20-25 mm, between about 25-30 mm, between about 30-35 mm, between about 35-40 mm, between about 45-50 mm, between about 50-55 mm, or between about 55-60 mm.

Figure 23:
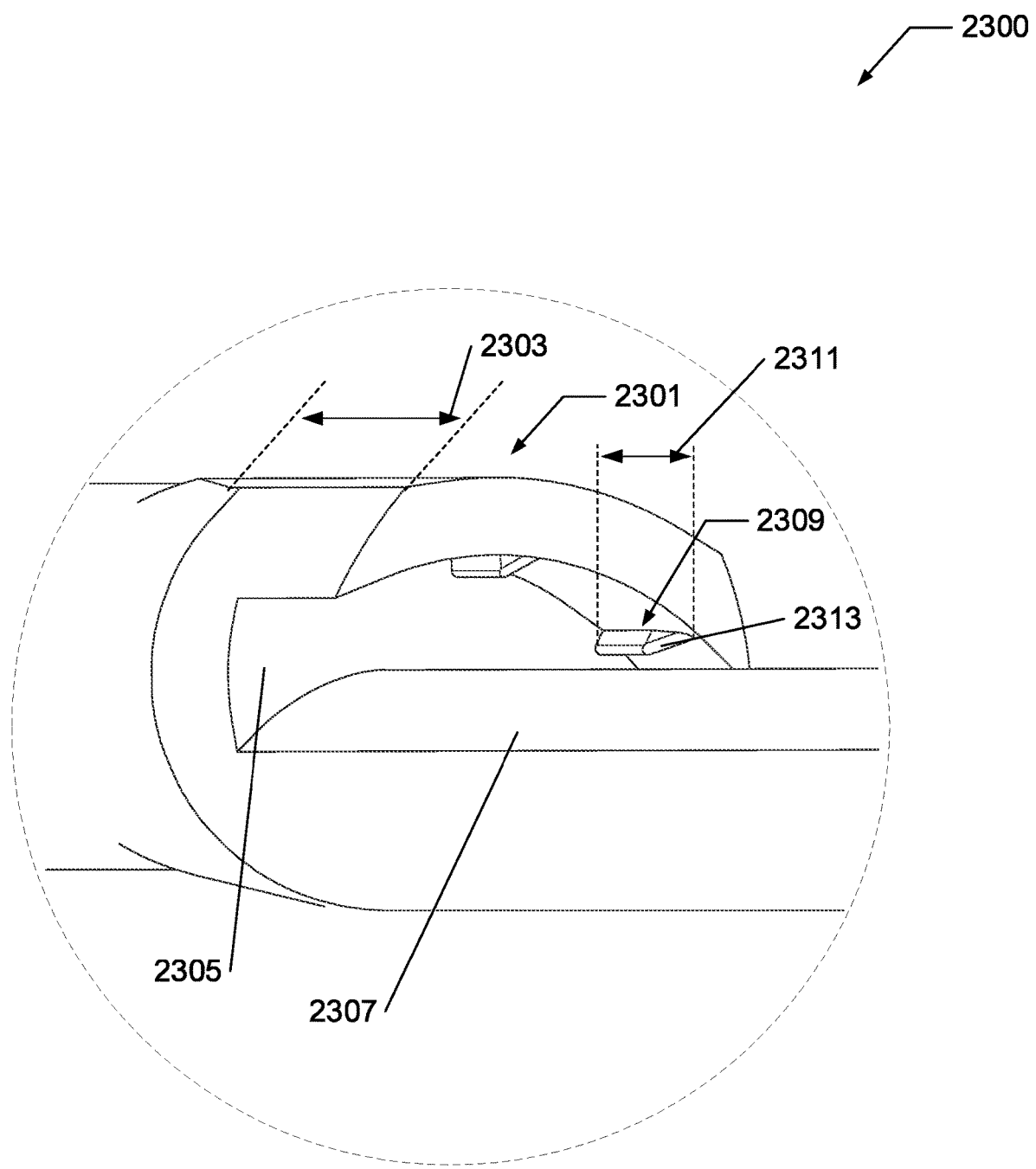
FIG. 23 is a partial perspective view of an exemplary pedicle insulator inserter, according to one embodiment.

FIG. 23 illustrates an inserter recess 2300 of a pedicle insulator inserter. In various embodiments, the recess 2300 houses and secures a pedicle insulator within the inserter. In one or more embodiments, the recess 2300 includes an overhang 2301. In at least one embodiment the overhang 2301 includes an overhang length 2303 which may measure between about 3.0-5.0 mm. In various embodiments, the overhang length 2301 may measure between about 2.5-3.0 mm, between about 3.0-3.5 mm, between about 3.5-4.0 mm, between about 4.0-4.5 mm, between about 4.5-5.0 mm, or between about 5.0-5.5 mm.

In various embodiments, the recess 2300 includes a back-plate 2305. In at least one embodiment, the back-plate 2305 may include a geometric profile that is substantially congruous to a geometric profile of the top of a pedicle insulator (e.g., as illustrated in FIG. 11). Thus, in one or more embodiments, the top of a pedicle insulator that has been loaded into the inserter (e.g., and slid into the recess 2300) may be in substantially conformed contact with the back-plate 2305.

In one or more embodiments, the recess 2300 includes a loading surface 2307 that may also form a surface of the inserter secondary shaft (e.g., as illustrated in FIG. 22). In at least one embodiment, the loading surface 2307 may include a geometric profile that is substantially congruous to a geometric profile of the back of a pedicle insulator (e.g., as can be observed in FIG. 8). Thus, in various embodiments, the back of a pedicle insulator that has been loaded into the inserter may be in substantially conformed contact with the loading surface 2307.

In various embodiments, the recess 2300 includes a fin 2309 (e.g., one or more fins 2309). In at least one embodiment, the fin 2309 provides frictional forces to secure loading of a pedicle insulator into the inserter (e.g., more specifically, into the recess 2300). In one or more embodiments, the recess 2300 includes a plurality of fins 2309 (such as, for example, between about 2-20). In some embodiments, the fin 2309 includes a fin length 2311 that may measure between about 1-3 mm. In at least one embodiment the fin length 2311 may measure between about 0.01-0.1 mm, between about 0.1-0.3 mm, between about 0.3-0.5 mm, between about 0.5-0.7 mm, between about 0.7-0.9 mm, between about 0.9-1.1 mm, between about 1.1-1.3 mm, between about 1.3-1.5 mm, between about 1.5-1.7 mm, between about 1.7-1.9 mm, between about 1.9-2.1 mm, between about 2.1-2.3 mm, between about 2.3-2.5 mm, between about 2.5-2.7 mm, between about 2.7-2.9 mm, between about 2.9-3.1 mm, or between about 3.1-3.3 mm.

In various embodiments, the fin 2309 includes a tapered surface 2313. In at least one embodiment, the tapered surface 2313 guides loading of a pedicle insulator into the recess 2300. In various embodiments, upon and after loading, one or more fins 2309 press the pedicle insulator into the loading surface 2307, thereby generating frictional forces that secure the pedicle insulator within the recess 2300 and atop the loading surface 2307. Thus, the pedicle insulator may be secured within the recess 2300 and atop the loading surface 2307 by means of a press fit initiated and maintained by the one or more fins 2309.

Figure 24:
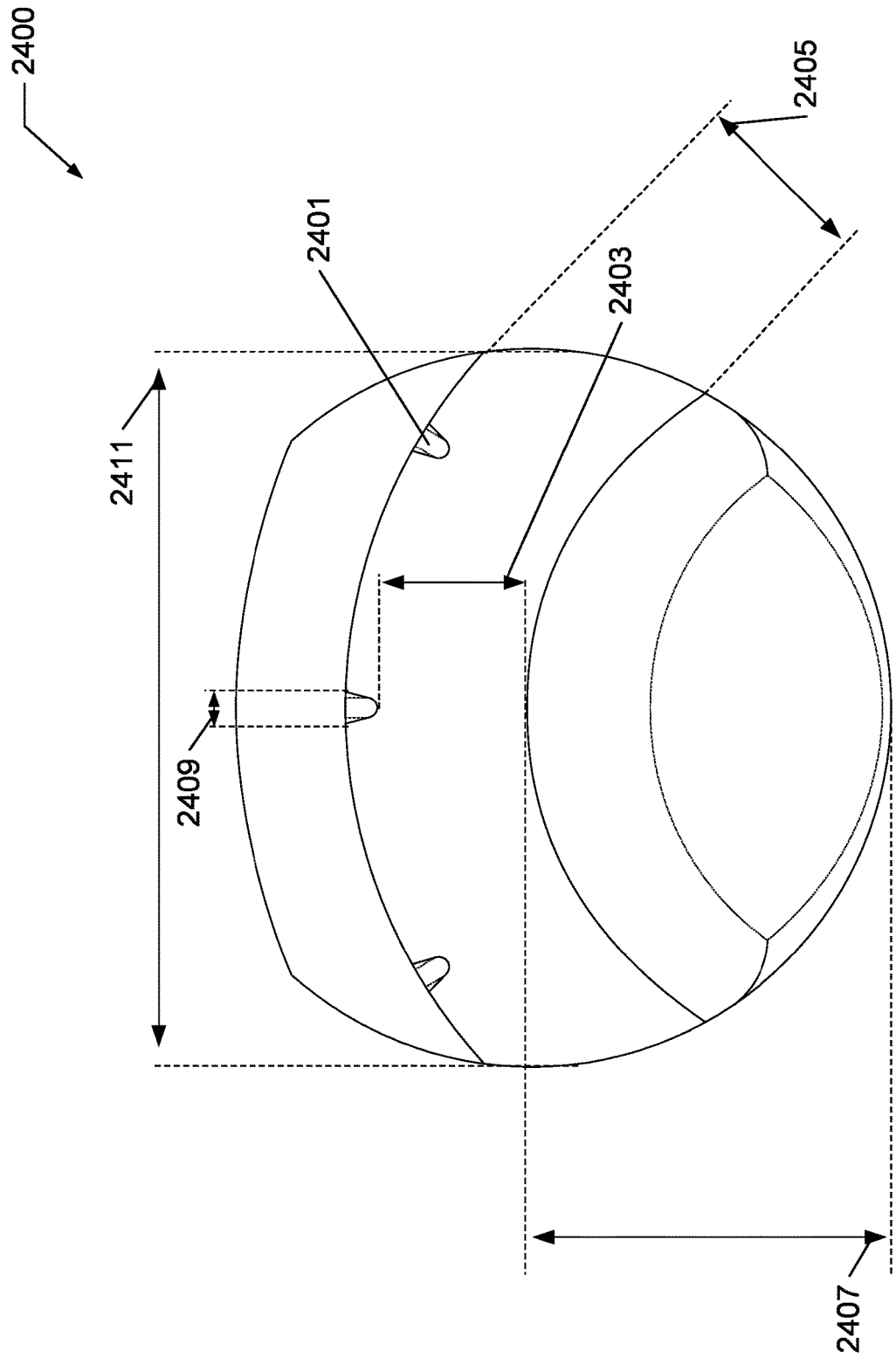
FIG. 24 is a bottom view of an exemplary pedicle insulator inserter, according to one embodiment.

FIG. 24 illustrates a pedicle insulator inserter 2400. In one or more embodiments, the inserter 2400 includes a fin 2401 and a first fin distance 2403. In at least one embodiment, the first fin distance 2403 may represent a distance between a bottom of the fin 2401 and a loading surface (as illustrated in FIG. 23). In various embodiments, the first fin distance 2403 may measure between about 1-1.5 mm. In at least one embodiment the first fin distance 2403 may measure between about 0.7-0.8 mm, between about 0.8-0.9 mm, between about 0.9-1.0 mm, between about 1.0-1.1 mm, between about 1.2-1.3 mm, between about 1.4-1.5 mm, between about 1.5-1.6 mm, between about 1.7-1.8 mm, between about 1.8-1.9 mm, between about 1.9-2.0 mm, or between about 2.0-2.1 mm. In some embodiments, a magnitude of the first fin distance 2403 may be determined by and substantially conform to an outer radius of a pedicle insulator (for example, outer radius 1119 illustrated in FIG. 11). In one or more embodiments, the fin distance 2403 may be sized in a manner such that one or more fins 2401 generate frictional forces of a specific magnitude upon receipt of a pedicle insulator into the inserter 2400 (e.g., into a recess of the inserter 2400). In at least one embodiment, the fin distance 2403 may be sized in a manner such that the generated frictional forces are of a magnitude that is less than a magnitude of an a force generated by one or more fixation features (e.g., teeth and ridges described herein) of a deployed pedicle insulator in response to a pullout force. Thus, the fin distance 2403 may be sized such that the pedicle insulator is held securely in place, but may be dislodged from the inserter 2400 (e.g., by means of a pullout force and corresponding opposing force) upon deployment into a target site.

In various embodiments, the inserter 2400 further includes a second fin distance 2405 that may represent a distance between a top of the fin 2401 and the loading surface. In at least one embodiment, the second fin distance 2405 may measure between about 1-2 mm. In at least one embodiment the second fin distance 2405 may measure between about 0.9-1.0 mm, between about 1.0-1.1 mm, between about 1.1-1.2 mm, between about 1.2-1.3 mm, between about 1.3-1.4 mm, between about 1.4-1.5 mm, between about 1.5-1.6 mm, between about 1.7-1.8 mm, between about 1.8-1.9 mm, or between about 1.9-2.0 mm. In one or more embodiments, the second fin distance 2405 may be determined by a thickness of a pedicle insulator. In at least one embodiment, the second fin distance 2405 may be sized in a manner such that a recess and the loading surface of the inserter 2400 may accommodate a pedicle insulator. Thus, in various embodiments, the second fin distance 2405 may be sized in a manner such that a pedicle insulator may be loaded into a recess of the inserter 2400, but also (upon being loaded) engage in a frictional interaction with one or more fins 2401 to secure the pedicle insulator within the recess and atop a loading surface.

In various embodiments, the inserter 2400 includes a radius 2407. In one or more embodiments, the radius 2407 may measure between about 2-4 mm. In at least one embodiment the radius 2407 may measure between about 1.7-2.0 mm, between about 2.0-2.3 mm, between about 2.3-2.7 mm, between about 2.7-3.0 mm, between about 3.0-3.3 mm, between about 3.3-3.7 mm, between about 3.7-4.0 mm, or between about 4.0-4.3 mm. In at least one embodiment, a magnitude of the radius 2407 may be determined by, and substantially conform to, an outer radius of a pedicle insulator. In various embodiments, the fin 2401 includes a fin width 2409 that may measure between about 0.1-1 mm. In at least one embodiment the fin width 2409 may measure between about 0.01-0.1 mm, between about 0.1-0.2 mm, between about 0.2-0.3 mm, between about 0.4-0.5 mm, between about 0.5-0.6 mm, between about 0.6-0.7 mm, between about 0.7-0.8 mm. between about 0.8-0.9 mm, between about 0.9-1.0 mm, or between about 1.0-1.1 mm. In one or more embodiments, the inserter 2400 further includes a secondary shaft width 2411. In at least one embodiment, the width 2411 may refer to a width of an inserter secondary shaft (e.g., as illustrated in FIG. 22) and a width of an inserter recess (e.g., as illustrated in FIG. 23).

Figure 25:
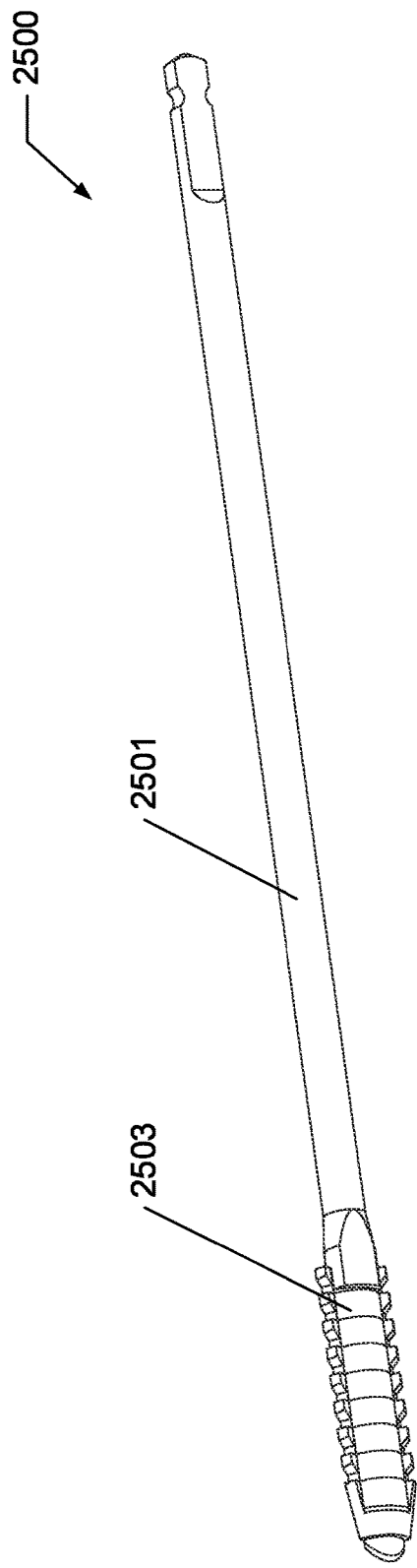
FIG. 25 is a perspective view of an exemplary pedicle insulator and inserter, according to one embodiment.

FIG. 25 illustrates a pedicle insulator apparatus 2500. In various embodiments, the apparatus 2500 includes an inserter 2501 and a pedicle insulator 2503. In one or more embodiments, the pedicle insulator 2503 is secured on a loading surface and within a recess of the inserter 2501. In at least one embodiment, the apparatus 2500 may be provided to a user (e.g., a surgeon) as shown (e.g., with the insulator 2503 already loaded). In some embodiments, the apparatus 2500 may be provided to the user as part of a kit, the kit further including an additional 2-20 insulators 2503 (e.g., which may be loaded into the inserter 2501 and delivered to one or more target sites throughout a surgery). In at least one embodiment, the kit and apparatus 2500 may be subject to one or more sterilization treatments (e.g., prior to being provided to a user).

Figure 26:
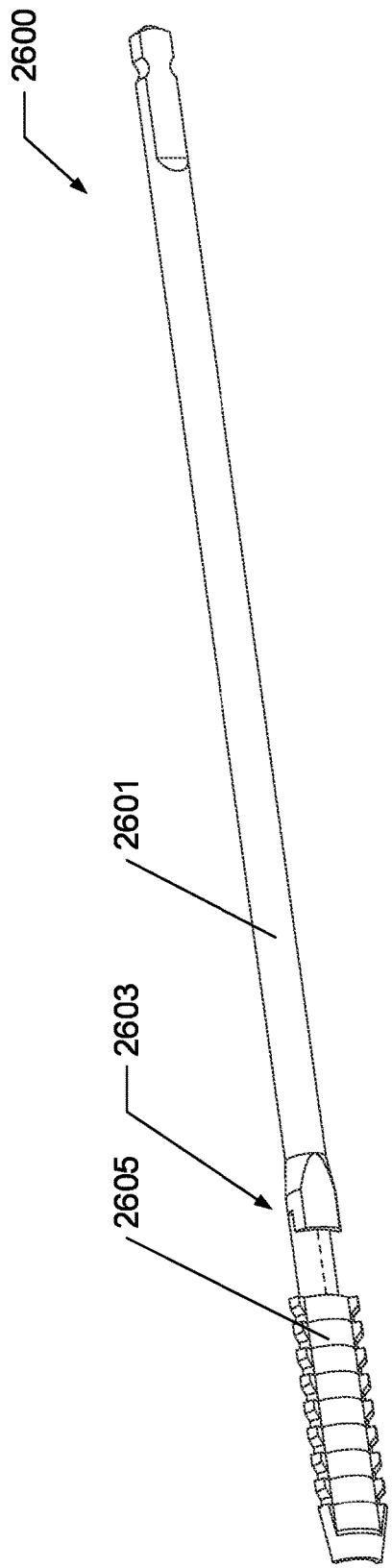
FIG. 26 is a perspective view of an exemplary pedicle insulator and inserter, according to one embodiment.
Figure 27:
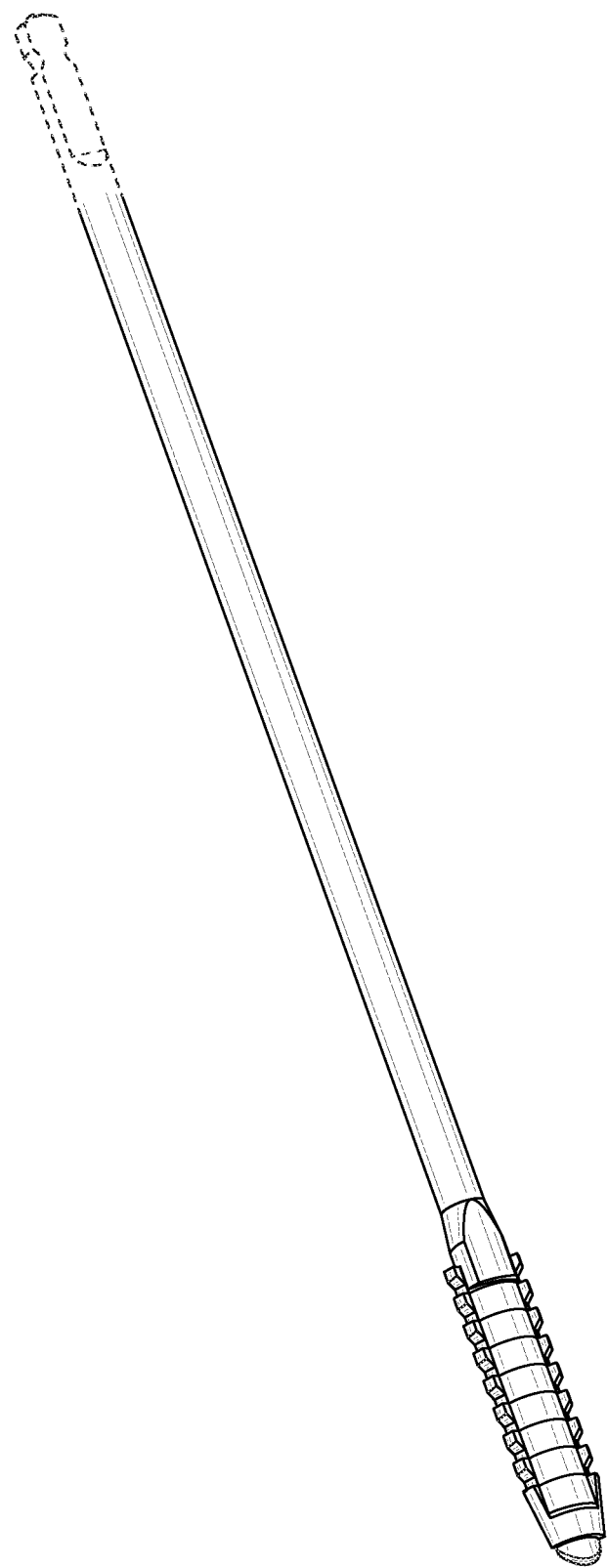
FIG. 27 is a perspective view of an exemplary pedicle insulator and inserter, according to one embodiment.
Figure 28:
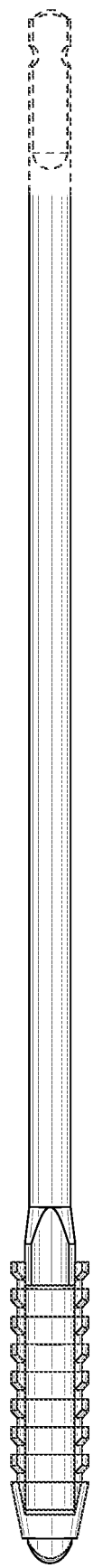
FIG. 28 is a top view of an exemplary pedicle insulator and inserter, according to one embodiment.
Figure 29:
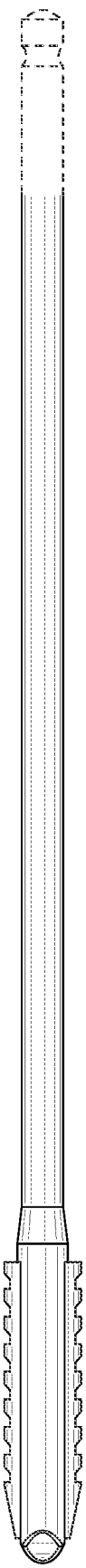
FIG. 29 is a bottom view of an exemplary pedicle insulator and inserter, according to one embodiment.
Figure 30:
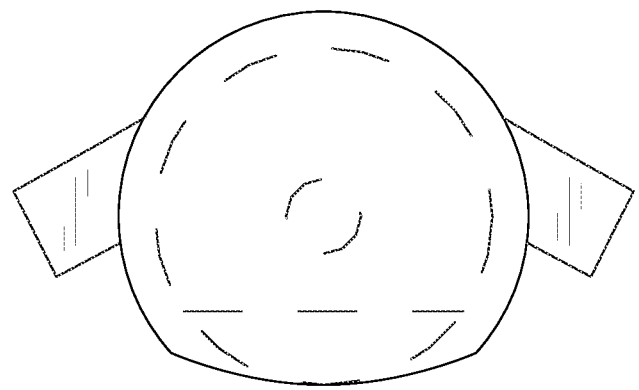
FIG. 30 is a back view of an exemplary pedicle insulator and inserter, according to one embodiment.
Figure 31:
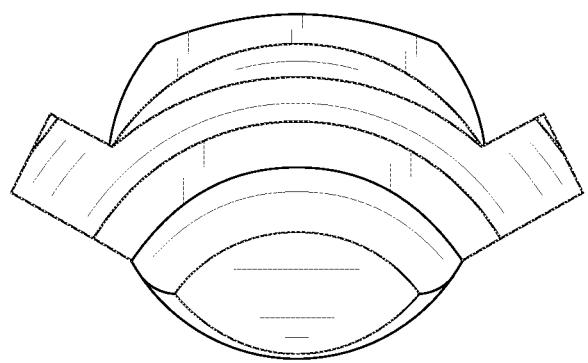
FIG. 31 is a front view of an exemplary pedicle insulator and inserter, according to one embodiment.
Figure 32:
FIG. 32 is a side view of an exemplary pedicle insulator and inserter, according to one embodiment.
Figure 33:
FIG. 33 is a side view of an exemplary pedicle insulator and inserter, according to one embodiment.

FIG. 26 illustrates a pedicle insulator apparatus 2600. In one or more embodiments, the apparatus 2600 includes an inserter 2601 and a pedicle insulator 2605. In at least one embodiment, a user deploys the insulator 2605 from the inserter 2601 by sliding the insulator 2605 from a recess 2603 located within a secondary shaft of the inserter 2601. For example, a user may orient the apparatus 2600 within a target site and apply a pulling force (e.g., to dislodge and deploy the insulator 2605 from the recess 2603 and inserter 2601). In the same example, one or more teeth sections and other fixations features (e.g., described earlier herein) may provide a resistive force (e.g., in opposition to the pulling force) sufficient to dislodge the insulator 2605 from the recess 2603 and, thereby, deploy the insulator 2605 to the target site.

FIGS. 27-31 illustrate additional embodiments of a pedicle insulator inserter described herein. In at least one embodiment, the pedicle insulator inserter illustrated in FIGS. 27-31 may be the same or substantially similar to the pedicle insulator inserter illustrated in FIGS. 15-26. As described herein, a pedicle insulator may be secured to the inserter and delivered to, on, or within a body.

CONCLUSION

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence (s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

I claim:

1. An implant for stabilizing a surgical fixture comprising:
    an elongate body formed about an axis of revolution, wherein the elongate body further comprises
        a proximal end;
        a distal end;
        a channel surface extending an entire distance between the proximal and distal ends;
        a ridged surface opposite the channel surface extending between the proximal and distal ends comprising one or more ridges, wherein the ridged surface is symmetrically oriented along the axis of revolution;
        a first longitudinal runner and a second longitudinal runner adjacent the channel surface and extending between the proximal and distal ends;
        a first teeth section extending outwardly from the first longitudinal runner comprising one or more teeth; and
        a second teeth section extending outwardly from the second longitudinal runner comprising one or more teeth, wherein the radial distance between the axis of revolution to the outermost point of the one or more teeth is greater than the radial distance between the axis of revolution and the apex of the one or more ridges.

2. The implant of claim 1, wherein the channel surface is configured to receive a surgical implant.

3. The implant of claim 2, wherein the implant is a pedicle screw.

4. The implant of claim 1, wherein the ridges have an elliptical profile.

5. The implant of claim 1, wherein the tooth height of at least one of the teeth as measured from the runner is between 0.5 mm and 5 mm.

6. The implant of claim 1, wherein the shape of the teeth is different from the shape of the ridges.

7. The implant of claim 1, wherein the longitudinal width of the teeth is less than the longitudinal width of the ridges.

8. An implant for stabilizing a surgical fixture comprising:
    an elongate body having a semi-cylindrical shape about its entire longitude, the elongate body further comprising:
        a proximal end;
        a distal end;
        a channel surface extending an entire distance between the proximal and distal ends having a first longitudinal edge and a second longitudinal edge;
        a first runner surface adjacent to the first longitudinal edge and a second runner surface adjacent to the second longitudinal edge;
        a ridged surface opposite the channel surface and extending between the proximal and distal ends wherein the ridge section comprises one or more ridges having a first geometry;
        a first teeth section extending outwardly from the first runner surface wherein the first teeth section comprises one or more teeth having a second geometry; and
        a second teeth section extending outwardly from the second runner surface wherein the second tooth section comprises one or more teeth having a third geometry;
    wherein the second and third geometries are different from the first geometry.

9. The implant of claim 8, wherein the first and second teeth sections have the same geometry.

10. The implant of claim 8, wherein the teeth in the first and second teeth sections have a smaller longitudinal width than the ridges within the ridge section.

11. The implant of claim 8, wherein the first and second teeth sections have a greater radial height than the ridge section.

12. The implant of claim 8, wherein the faces of the teeth closest the distal end of the implant are at a different angle form the faces of the ridges closest to the distal end of the implant relative to the channel surface.

13. The implant of claim 12, wherein the faces of the teeth closest to the distal end of the implant do not align with the faces of the ridges closest to the distal end of the implant.

14. The implant of claim 12, wherein the faces of the teeth closest to the proximal end of the implant align with the faces of the ridges closest to the proximal end of the implant.

15. An implant for stabilizing a surgical fixture comprising:
    a elongate body of revolution, being revolved about an axis of revolution no more than 180 degrees and having a thickness, wherein the body further comprises:
        a proximal end;
        a distal end;
        a channel surface formed on a face of the body nearest the axis of revolution, the channel surface extending an entire distance between the proximal and distal end;
        one or more ridges formed on a face of the body furthest from the axis of revolution; and
        one or more teeth formed at the longitudinal edges of the body and extending away from the axis of revolution,
        wherein the teeth further comprise a first side surface adjacent to the channel and a second side surface opposite the first side surface that forms a crease with the ridge section.

16. The implant of claim 15, wherein the height of the teeth from the body of revolution is greater than the height of the ridges from the body of revolution.

17. The implant of claim 15, wherein the teeth further comprise a sloping surface.

18. The implant of claim 17, wherein the sloping surface of the teeth is nearest the distal end.

19. The implant of claim 18, wherein the ridges comprise a sloping surface and the angle of the sloping surface of the ridges is different from the angle of the sloping surface of the teeth.

20. The implant of claim 19, wherein the teeth and the ridges further comprise a flat surface normal to the channel surface.

\* \* \* \* \*